(12) United States Patent
Moshos et al.

(10) Patent No.: US 9,695,196 B2
(45) Date of Patent: Jul. 4, 2017

(54) REACTIONS OF THIADIAZOLYL-OXIMINOACETIC ACID DERIVATIVE COMPOUNDS

(71) Applicant: Merck Sharp & Dohme Corp., Rahway, NJ (US)

(72) Inventors: Kristos Adrian Moshos, Belmont, MA (US); Valdas Jurkauskas, Cambridge, MA (US); Manuel Scanu, Milan (IT); Michele Benotti, Pavia (IT)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/319,104

(22) PCT Filed: Jun. 19, 2015

(86) PCT No.: PCT/US2015/036704
§ 371 (c)(1),
(2) Date: Dec. 15, 2016

(87) PCT Pub. No.: WO2015/196077
PCT Pub. Date: Dec. 23, 2015

(65) Prior Publication Data
US 2017/0129906 A1    May 11, 2017

Related U.S. Application Data

(60) Provisional application No. 62/014,884, filed on Jun. 20, 2014.

(51) Int. Cl.
*C07D 501/04*    (2006.01)
*C07D 285/08*    (2006.01)

(52) U.S. Cl.
CPC ......... *C07D 501/04* (2013.01); *C07D 285/08* (2013.01)

(58) Field of Classification Search
CPC .................... C07D 501/04; C07D 285/08
See application file for complete search history.

(56) References Cited

U.S. PATENT DOCUMENTS

| | | | |
|---|---|---|---|
| 5,108,997 A * | 4/1992 | Takaya | C07D 501/46 514/202 |
| 7,192,943 B2 | 3/2007 | Yamanaka et al. | |
| 2004/0242929 A1 | 12/2004 | Shiigi | |
| 2005/0096306 A1 | 5/2005 | Yamanaka et al. | |
| 2013/0065874 A1 | 3/2013 | Chandorkar et al. | |

FOREIGN PATENT DOCUMENTS

WO    2014152763 A1    9/2014

OTHER PUBLICATIONS

Toda et al., "Synthesis and SAR of novel parenteral antipseudomonal cephalosporins: Discovery of FR264205", Bioorg. Med. Chem. Lett., 18, 4849-4852 (2008).
International Search Report and Written Opinion for PCT/US2015/036704 dated Sep. 15, 2015.

* cited by examiner

*Primary Examiner* — Matthew Coughlin
(74) *Attorney, Agent, or Firm* — J. Eric Thies; John C. Todaro

(57) ABSTRACT

This disclosure relates to an improved synthesis of cephalosporin antibiotic compounds such as ceftolozane, and compositions and methods of use thereof. Thiadiazolyl-oximinoacetic acid compounds such as TATD can be reacted to yield the activated thiadiazolyl-oximinoacetic acid methanesulfonate ester compounds useful in the manufacture of cephalosporin antibiotic compounds.

33 Claims, 15 Drawing Sheets

Figure 3

| Samples | Selected parameters | | | | | | TATD-Ms IPC (% conversion) 1hr/2hr/3hr | Comments |
|---|---|---|---|---|---|---|---|---|
| | TATD (eq.) | Methanesulfonyl chloride (eq.) | K₂CO₃ (eq.) | K₂CO₃ (mesh size) | K₂CO₃ D90 (μm) | Rxn. Temp. (°C) | | |
| 1 | 0.9 | 2.6 | 1.3 | <400 | 27 | -5 | 99.2/99.2/99.0 | Reaction becomes very viscous, difficult to agitate |
| 2 | 0.9 | 1.8 | 0.9 | <400 | 27 | -5 | 99.1/99.2/99.1 | Reaction becomes very viscous, difficult to agitate |
| 3 | 0.9 | 1.8 | 1.3 | <400 | 27 | 20 | 97.4/96.5/91.6 | Reaction becomes very viscous, difficult to agitate |
| 4 | 0.9 | 2.6 | 0.9 | <400 | 27 | 20 | 98.5/96.6/94.2 | Reaction becomes very viscous, difficult to agitate |
| 5 | 1.3 | 1.8 | 1.3 | <400 | 27 | -5 | 98.3/95.0/90.6 | Product unstable and degrades, poor yield |
| 6 | 1.3 | 2.6 | 1.3 | <400 | 27 | 20 | 97.4/95.7/92.3 | Become to a gel, IPC may not representative |
| 7 | 1.3 | 1.8 | 0.9 | <400 | 27 | 20 | 97.9/95.5/88.8 | Reaction becomes very viscous, difficult to agitate |
| 8 | 1.3 | 2.6 | 0.9 | <400 | 27 | -5 | 99.1/99.1/98.7 | Reaction becomes very viscous, difficult to agitate |
| 9 | 1.1 | 2.2 | 1.1 | 120-200 | 228 | 7.5 | 99.6/99.5/99.5 | Good yield and purity |
| 10 | 1.1 | 2.2 | 1.1 | 120-200 | 228 | 7.5 | 99.6/99.5/99.4 | Good yield and purity |
| 11 | 1.1 | 2.2 | 1.1 | 120-200 | 228 | 7.5 | 99.6/99.5/99.5 | Good yield and purity |
| 12 | 1.1 | 2.2 | 1.1 | 120-200 | 228 | 7.5 | 99.6/99.5/99.5 | Good yield and purity |
| 13 | 0.9 | 2.6 | 0.9 | 35-80 | 497 | -5 | 30.2/51.6/62.9 | Slow conversion, reaction stalls, poor yield |
| 14 | 0.9 | 2.6 | 1.3 | 35-80 | 497 | 20 | 57.3/56.5/54.8 | Slow conversion, reaction stalls, poor yield |
| 15 | 0.9 | 1.8 | 0.9 | 35-80 | 497 | 20 | 38.4/40.7/40.1 | Slow conversion, reaction stalls, poor yield |
| 16 | 0.9 | 1.8 | 1.3 | 35-80 | 497 | -5 | 64.2/85.9/95.4 | Slow conversion, reaction stalls, poor yield |
| 17 | 1.3 | 1.8 | 0.9 | 35-80 | 497 | -5 | 22.7/40.8/52.1 | Slow conversion, reaction stalls, poor yield |
| 18 | 1.3 | 2.6 | 1.3 | 35-80 | 497 | -5 | 40.5/65.4/77.4 | Slow conversion, reaction stalls, poor yield |
| 19 | 1.3 | 2.6 | 0.9 | 35-80 | 497 | 20 | 42.4/42.6/41.1 | Slow conversion, reaction stalls, poor yield |
| 20 | 1.3 | 1.8 | 1.3 | 35-80 | 497 | 20 | 57.6/67.0/66.9 | Slow conversion, reaction stalls, poor yield |

Figure 4

| Samples | Selected parameters | | | | | | Responses | | Comments |
|---|---|---|---|---|---|---|---|---|---|
| | TATD (eq.) | Methanesulfonyl chloride (eq.) | $K_2CO_3$ (eq.) | $K_2CO_3$ (mesh size) | $K_2CO_3$ D90 (μm) | Rxn. Temp. (°C) | TATD-Ms IPC (% conversion) 0.5hr/1hr/1.5hr | Max.Temp spike (°C) | |
| 1 | 1.3 | 2.6 | 0.9 | 230-270 | 36 | -5 | 99.1/99.3/99.4 | -3.5 | High yield, purity, easy to stir |
| 2 | 1.3 | 2.6 | 1.3 | 230-270 | 36 | 20 | 98.6/97.1/97.8 | 31 | Reaction viscosity prevented stirring |
| 3 | 1.3 | 1.8 | 0.9 | 230-270 | 36 | 20 | 99.2/98.9/98.3 | 24 | Reaction viscosity made stirring difficult |
| 4 | 0.9 | 1.8 | 0.9 | 230-270 | 36 | -5 | 98.7/99.3/99.3 | -4 | High yield, purity, easy to stir |
| 5 | 1.3 | 1.8 | 1.3 | 230-270 | 36 | -5 | 98.2/98.7/98.4 | -1 | High yield, purity, easy to stir |
| 6 | 0.9 | 2.6 | 1.3 | 230-270 | 36 | -5 | 99.2/99.3/99.4 | -2 | High yield, purity, easy to stir |
| 7 | 0.9 | 1.8 | 1.3 | 230-270 | 36 | 20 | 99.3/99.1/98.9 | 30 | Reaction viscosity prevented stirring |
| 8 | 0.9 | 2.6 | 0.9 | 230-270 | 36 | 20 | 99.6/99.1/98.2 | 26 | Reaction viscosity made stirring difficult |
| 9 | 1.1 | 2.2 | 1.1 | 170-200 | 124 | 7.5 | 99.6/99.6/99.6 | 9.5 | High yield, purity, easy to stir |
| 10 | 1.1 | 2.2 | 1.1 | 170-200 | 124 | 7.5 | 99.6/99.6/99.6 | 9.5 | High yield, purity, easy to stir |
| 11 | 1.1 | 2.2 | 1.1 | 170-200 | 124 | 7.5 | 99.4/99.6/99.5 | 9.5 | High yield, purity, easy to stir |
| 12 | 1.1 | 2.2 | 1.1 | 170-200 | 124 | 7.5 | 98.8/99.4/99.6 | 9.5 | High yield, purity, easy to stir |
| 13 | 0.9 | 1.8 | 1.3 | 80-100 | 249 | -5 | 48.3/99.3/99.7 | -5 | High yield, purity, easy to stir |
| 14 | 1.3 | 1.8 | 0.9 | 80-100 | 249 | -5 | 11.3/62.7/90.1 | -5 | Slow conversion, risk of failure |
| 15 | 1.3 | 2.6 | 1.3 | 80-100 | 249 | -5 | 29.7/86.0/98.7 | -5 | Slow conversion, risk of failure |
| 16 | 1.3 | 1.8 | 1.3 | 80-100 | 249 | 20 | 94.6/98.9/98.9 | 20 | High yield, purity, easy to stir |
| 17 | 0.9 | 2.6 | 1.3 | 80-100 | 249 | 20 | 98.0/99.2/99.2 | 20 | High yield, purity, easy to stir |
| 18 | 0.9 | 2.6 | 0.9 | 80-100 | 249 | -5 | 17.9/60.4/89.4 | -5 | Slow conversion, low yield and purity |
| 19 | 1.3 | 2.6 | 0.9 | 80-100 | 249 | 20 | 62.3/76.3/76.8 | 20 | Low yield and purity |
| 20 | 0.9 | 1.8 | 0.9 | 80-100 | 249 | 20 | 64.6/90.9/94.5 | 20 | Slow conversion, risk of failure |

REACTIONS OF THIADIAZOLYL-OXIMINOACETIC ACID DERIVATIVE COMPOUNDS

1. CROSS REFERENCE TO RELATED APPLICATIONS

This application is a U.S. National Phase application under 35 U.S.C. §371 of PCT Application No. PCT/US2015/036704, filed Jun. 19, 2015, which claims priority under 35 U.S.C. §119(e) from U.S. Ser. No. 62/014,884, filed Jun. 20, 2014, the contents of which are incorporated by reference in their entirety.

2. TECHNICAL FIELD

This disclosure relates to the synthesis of chemical compounds, including the reaction of thiadiazolyl-oximinoacetic acid compounds to obtain activated thiadiazolyl-oximinoacetic acid methanesulfonate esters useful in manufacturing cephalosporin compounds such as ceftolozane.

3. BACKGROUND

Ceftolozane is a cephalosporin antibacterial agent, also referred to as CXA-101, FR264205, or by chemical names such as (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methyl ethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of compound (VI), in FIG. 1A, that can be formulated for intravenous administration or infusion.

Ceftolozane can be obtained using methods described in U.S. Pat. No. 7,192,943 and Toda et al., "Synthesis and SAR of novel parenteral anti-pseudomonal cephalosporins: Discovery of FR264205," Bioorganic & Medicinal Chemistry Letters, 18, 4849-4852 (2008), incorporated herein by reference in its entirety. Referring to FIGS. 1B and 1C, synthesis of ceftolozane is disclosed from the starting material thiadiazolyl-oximinoacetic acid (compound (I)) also referred to as TATD. Activation of carboxylic acid group of thiadiazolyl-oximinoacetic acid (compound (I)) is carried out by methanesulfonyl chloride and potassium carbonate in a conventional solvent such as N, N-dimethylacetamide to yield the activated thiadiazolyl-oximinoacetic acid methanesulfonate ester (Ib). The reaction of activated thiadiazolyl-oximinoacetic acid (compound (Ib)) and 7-aminocephem compound (II) is disclosed to yield compound (III), which can be further reacted with 4-[(N-Boc-aminoethyl)carbamoylamino]-1-methyl-5-tritylaminopyrazole (IV) to obtain ceftolozane intermediate compound (V). The ceftolozane intermediate (compound (V)) is globally deprotected using a mixture of trifluoroacetic acid (TFA) and anisole to yield ceftolozane trifluoroacetate compound (Vb), which is further crystallized from a mixture of sulfuric acid and wet isopropanol to afford ceftolozane sulfate (compound (VI)).

Given the multi-step process for making ceftolozane, there remains a need for approaches to performing individual steps in the synthesis of ceftolozane with desirably high yields (e.g., at least about 90%), as well as ceftolozane intermediates useful in the manufacture of ceftolozane. Most of the ceftolozane synthetic methods as referenced herein are based on optimizing the synthesis of the intermediates or changing the order of the reactants or intermediates added during the reaction. This can include, for example, activation of the thiadiazolyl-oximinoacetic acid (I) with phosphoryl chloride in a conventional solvent such as N, N-dimethylformamide to obtain an acid halide compound, which is further reacted with 7-aminocephem compound (II) followed by a series of subsequent reactions to obtain ceftolozane sulfate (compound (VI)) (see, e.g., U.S. Pat. No. 7,129,232). As disclosed in U.S. Pat. No. 7,192,943, activation of the thiadiazolyl-oximinoacetic acid (compound (I)) can also be carried out with methanesulfonyl chloride in a conventional solvent such as N, N-dimethylacetamide to obtain a acid halide compound, which is further reacted with 7-aminocephem compound (II) followed by series of reactions to obtain ceftolozane sulfate (compound (VI)).

There remains a need for improved methods for the synthesis of compounds (Ib) and compound (III) with desirably high yields for various reasons, including ceftolozane synthesis. In particular, there is need for methods providing a desirably high yield of the conversion of compound (I) into compound (Ib), and to control the yield of the intermediates such as compound (III), which can be used in the subsequent steps to manufacture ceftolozane sulfate (compound (VI)). Higher yield processes can reduce manufacturing costs associated with, for example, the starting material TATD compound (I), which can be commercially obtained as [(Z)-2-(5-amino-1,2,4-thiadiazol-3-yl)-2-(((1-(tert-butoxy)-2-methyl-1-oxopropan-2-yl)oxy)imino) acetic acid], (CAS 76028-96-1). Compound (I) can be an expensive starting material used during the manufacturing of ceftolozane sulfate, so it is desirable to identify synthetic processes that utilize lower equivalents of compound (I); however, greater guidance is needed to improve the yield of certain intermediates in the manufacture of ceftolozane. For example, one step of the process comprises synthesizing compound (III) by reacting compound (II) with compound (Ib), which is obtained via the activation of compound (I).

4. SUMMARY

Processes disclosed herein can be used in synthesizing compound (Ib) (also referred to as TATD-Ms) with improved yield, wherein at least about 90% of compound (I) (also referred to as TATD) is converted to compound (Ib). As disclosed herein, the conversion of compound (I) to compound (Ib) in the presence of methanesulfonyl chloride and potassium carbonate with a desired yield can be obtained by selecting certain parameters of the reaction, most preferably the diameter of potassium carbonate particles, but also including the relevant amounts of reactants (e.g., TATD compound (I), methanesulfonyl chloride, and potassium carbonate), and the reaction temperature. In one embodiment, compound (Ib) can be synthesized by the activation of the carboxylic acid group of thiadiazolyl-oximinoacetic acid (compound (I)) using methanesulfonyl chloride and potassium carbonate particles of a particular size. Such reactions can give desirably high yields of the product of compound (Ib) (e.g., at least about 90%).

Preferred processes disclosed herein include reacting compound (I) with methanesulfonyl chloride in the presence of an amount of potassium carbonate particles having a pre-determined D90 for particle size and at a temperature effective to obtain at least 90% conversion of compound (I) to compound (Ib). The invention is based in part on the discovery that ceftolozane can be prepared by a process comprising reacting compound (I) with methanesulfonyl chloride in the presence of potassium carbonate particles having a D90 of 70-250 micrometers to obtain compound (Ib). Processes disclosed herein can provide a composition comprising compound (I), methanesulfonyl chloride, and potassium carbonate particles having a D90 of 70-180 micrometers. Also, when the disclosed reaction is carried out on a large scale, the use of this reaction technique can be advantageous over conventional reaction conditions in terms of ease of reaction workup, purity, and product yield.

The processes for the conversion of compound (I) into compound (Ib) can be used in the manufacturing of novel cephalosporins such as ceftolozane (compound (VI)). A cephalosporin compound can be prepared from compound (Ib) via the synthetic schemes described herein. The synthetic routes disclosed herein can be applied to synthesis on a desired scale with appropriate adjustment of reaction sequence, reaction conditions, isolation/purification methods, and choice of solvents. Compound (Ib) can be used in the manufacturing of novel cephalosporins such as ceftolozane (compound (IV)) by reacting compound (Ib) with compound (II) to obtain compound (III), the process further comprising the step of reacting compound (III) with compound (IV) to obtain compound (V), which can be further converted into compound (VI).

Provided herein is a process comprising admixing a compound of formula (Z-I)

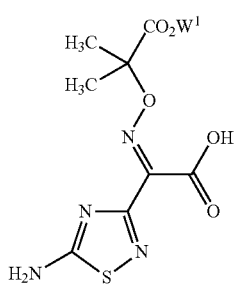
(Z-I)

with a compound of formula $R^SSO_2X^1$, in the presence of alkali metal carbonate particles having at least about 50% of the particles by weight in a range of from about 70 to about 250 micrometers, to obtain a compound of formula (Z-Ib-1)

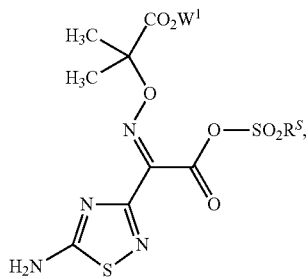
(Z-Ib-1)

wherein $W^1$ is an acid-labile protecting group; $X^1$ is Cl, Br, or I; and $R^S$ is a $C_1$-$C_6$ alkyl.

In some embodiments, the process comprises a process wherein the alkali metal carbonate particles have at least about 60%, at least about 70%, at least about 80%, or at least about 90% of the particles by weight in a range of from about 70 to about 250 micrometers. In some embodiments, the alkali metal carbonate is potassium carbonate.

In some embodiments, $W^1$ is tert-butyl.

In some embodiments, $R^S$ is $CH_3$.

In some embodiments, the molar equivalent ratio of the compound of formula (Z-I) to the alkali metal carbonate is in a range of from about 0.6 to about 1.4.

In some embodiments, the reaction temperature is in a range of from about −5 to about 20° C.

In some embodiments, $X^1$ is Cl.

In some embodiments, the molar equivalent ratio of the compound of formula $R^SSO_2X^1$ to the compound of formula (Z-I) is in a range of from about 1.3 to about 3.0.

In some embodiments, the process further comprises reacting the compound of formula (Z-Ib-1) with a compound of formula (Z-II):

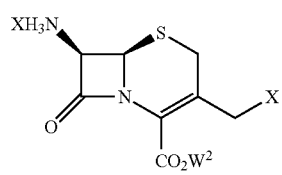
(Z-II)

to obtain a compound of formula (Z-III)

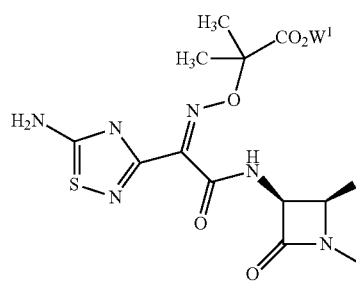
(Z-III)

wherein X is Cl, Br, or I; and $W^2$ is tert-butyl, para-methoxybenzyl, ortho-methoxybenzyl, or diphenylmethyl.

In some embodiments, the process further comprises the step of reacting compound (Z-III) with a compound of formula (Z-IV)

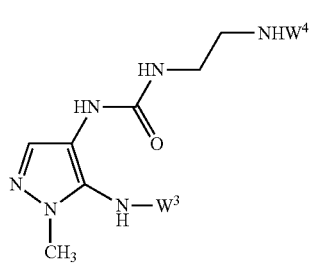
(Z-IV)

to obtain a compound of formula (Z-V)

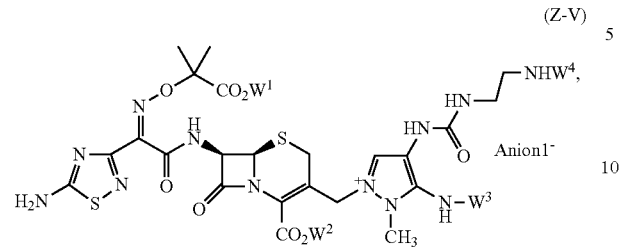
(Z-V)

wherein $W^3$ and $W^4$ are each independently triphenylmethyl, tert-butyl, tert-butoxycarbonyl, or para-methoxybenzoyl; and Anion1 is Cl, Br, I, trifluoroacetate, trifluoromethanesulfonate, or hydrogen sulfate.

In some embodiments, the process further comprises the step of converting a compound of formula (Z-V) to a compound of formula (Z-VI):

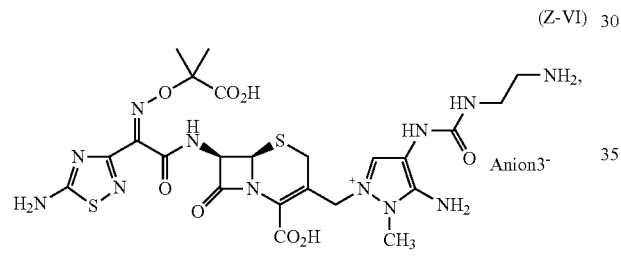
(Z-VI)

wherein Anion3 is Cl, Br, I, methanesulfonate, toluenesulfonate, hydrogen sulfate, or sulfate.

In some embodiments, the process comprises reacting compound (I)

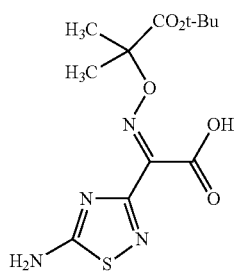
(I)

with methanesulfonyl chloride in the presence of potassium carbonate particles having a D90 of 70-250 micrometers, to obtain compound (Ib)

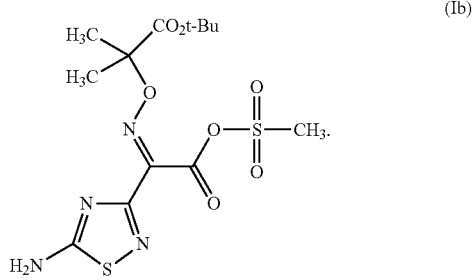 [SMILES: CC(C)(C)OC(=O)C(C)(C)O/N=C(\C(=O)OS(C)(=O)=O)c1nsc(N)n1]
(Ib)

In some embodiments, the process comprises a total of about 1.05 to 1.30 equivalents of potassium carbonate that are combined with compound (I).

In some embodiments, the process comprises a reaction of formula (I) that occurs in a solution at a temperature of about 0-13 degrees C.

In some embodiments, the process comprises a reaction wherein at least about 90% of compound (I) is converted to compound (Ib).

In some embodiments, the process further comprises the step of reacting compound (Ib) with compound (II)

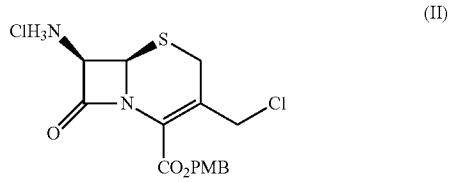
(II)

to obtain compound (III)

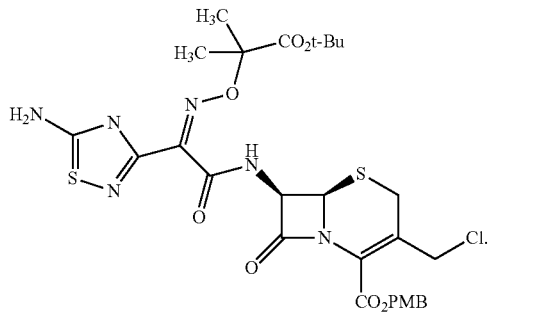
(III)

In some embodiments, the process further comprises the step of reacting compound (III) with compound (IV)

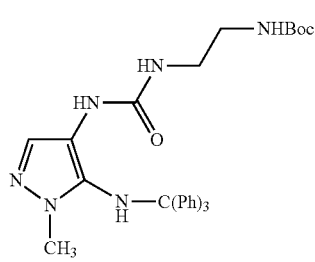

to obtain compound (V)

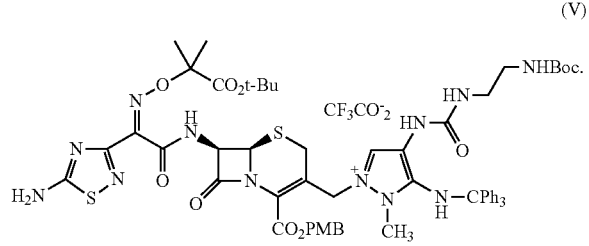

In some embodiments, the process further comprises the step of converting compound (V) to compound (VI)

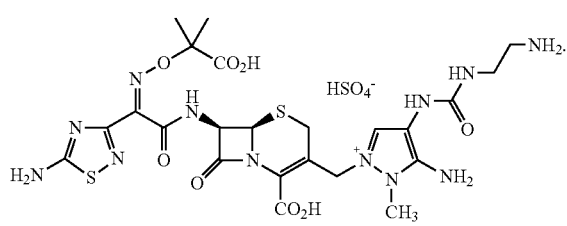

Further provided herein is a composition comprising compound (I), methanesulfonyl chloride and potassium carbonate particles having a D90 of 70-180 micrometers.

In some embodiments, the composition comprises a total of about 1.05 to 1.30 equivalents of potassium carbonate relative to the amount of compound (I).

In some embodiments, the composition has a temperature of about 0 to 15 degrees C.

In some embodiments, the composition further comprises compound (Ib).

Also provided is a process comprising reacting compound (I) with methanesulfonyl chloride in the presence of an amount of potassium carbonate particles having a predetermined D90 and at a temperature effective to obtain at least 90% conversion of compound (I) to compound (Ib).

In some embodiments, the reaction is performed at a temperature of about 0 to 15 degrees C.

In some embodiments, the reaction is performed without an increase in temperature of greater than about 10 degrees C.

In some embodiments, the reactants are maintained in contact for about 3 hours before isolating the compound (Ib).

In some embodiments, the process comprises a process wherein at least about 97% of compound (I) is converted to compound (Ib) within about 3 hours.

In some embodiments, the process comprises a process wherein the molar ratio of potassium carbonate to compound (I) is between about 1.05 and 1.30 in the reaction.

5. BRIEF DESCRIPTION OF THE DRAWINGS

FIG. 3 is a table of design of experiment (DOE) study of synthesis of TATD-Ms (compound (Ib)) (Version 2).

FIG. 4 is a table of design of experiment (DOE) study of synthesis of TATD-Ms (compound (Ib)) (Version 3).

Figure 7:
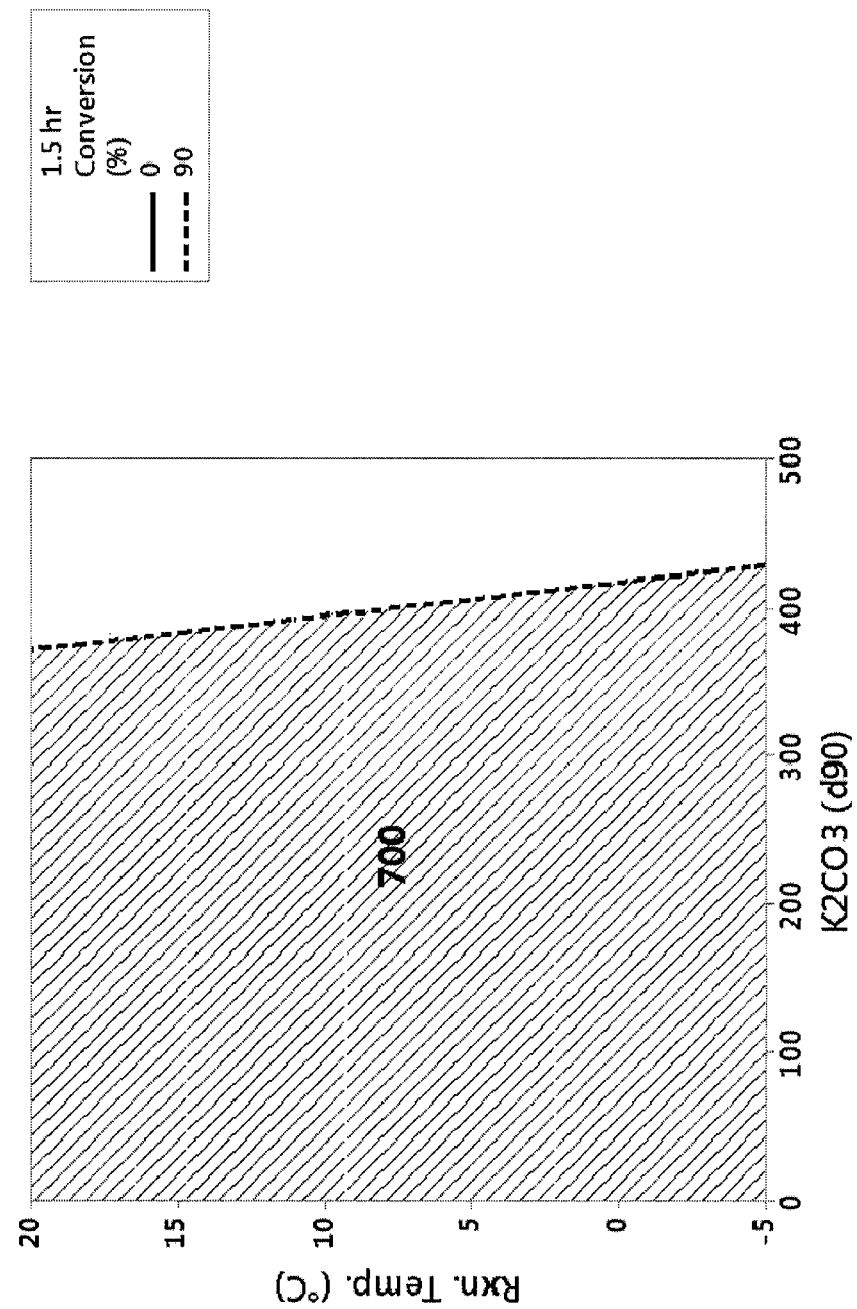

FIG. 7 is the contour plot of reaction conversion at 1.5 hours versus potassium carbonate particle size and reaction temperature. Y-axis shows reaction temperature in degrees Celsius ("Rxn. Temp. (° C.)"); x-axis shows the D90 values of potassium carbonate in micrometers ("K2CO3 (d90)").

Figure 8:
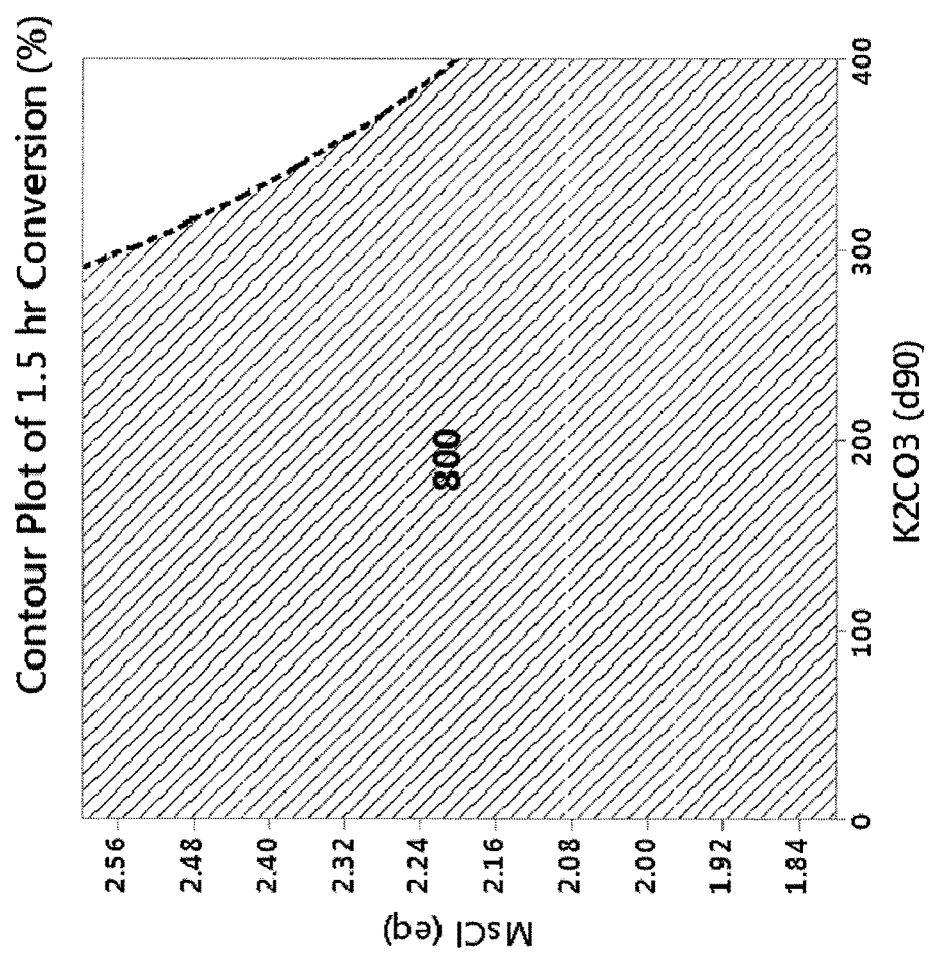

FIG. 8 is the contour plot of reaction conversion at 1.5 hours versus potassium carbonate particle size and methanesulfonyl chloride equivalents. Y-axis shows the number of equivalents of methanesulfonyl chloride ("MsCl (eq)") relative to compound (II); x-axis shows the D90 values of potassium carbonate in micrometers ("K2CO3 (d90)").

Figure 9:
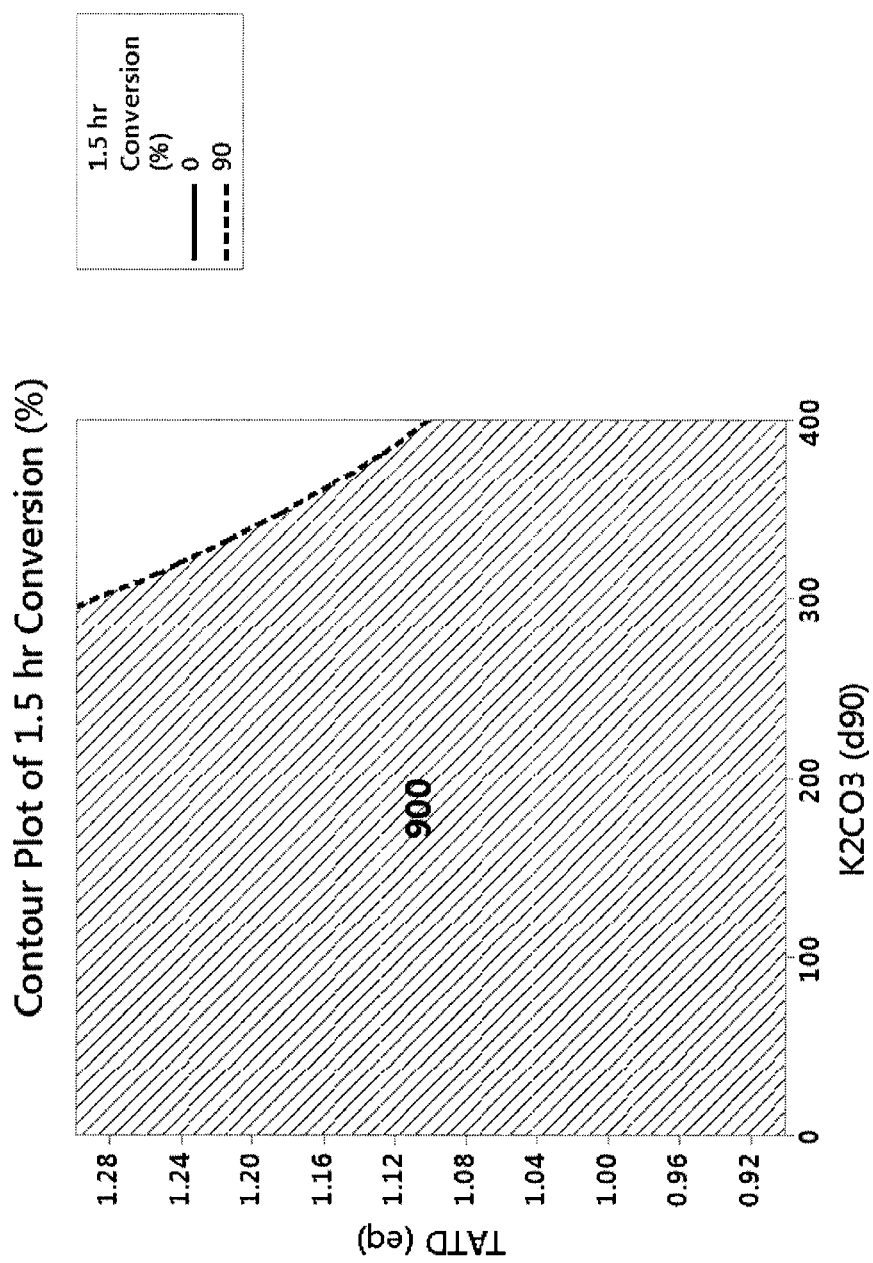

FIG. 9 is the contour plot of reaction conversion at 1.5 hours versus potassium carbonate particle size and TATD (compound (I)) equivalents. Y-axis shows the number of equivalents of compound (I) ("TATD (eq)") relative to compound (II); x-axis shows the D90 values of potassium carbonate in micrometers ("K2CO3 (d90)").

Figure 10:
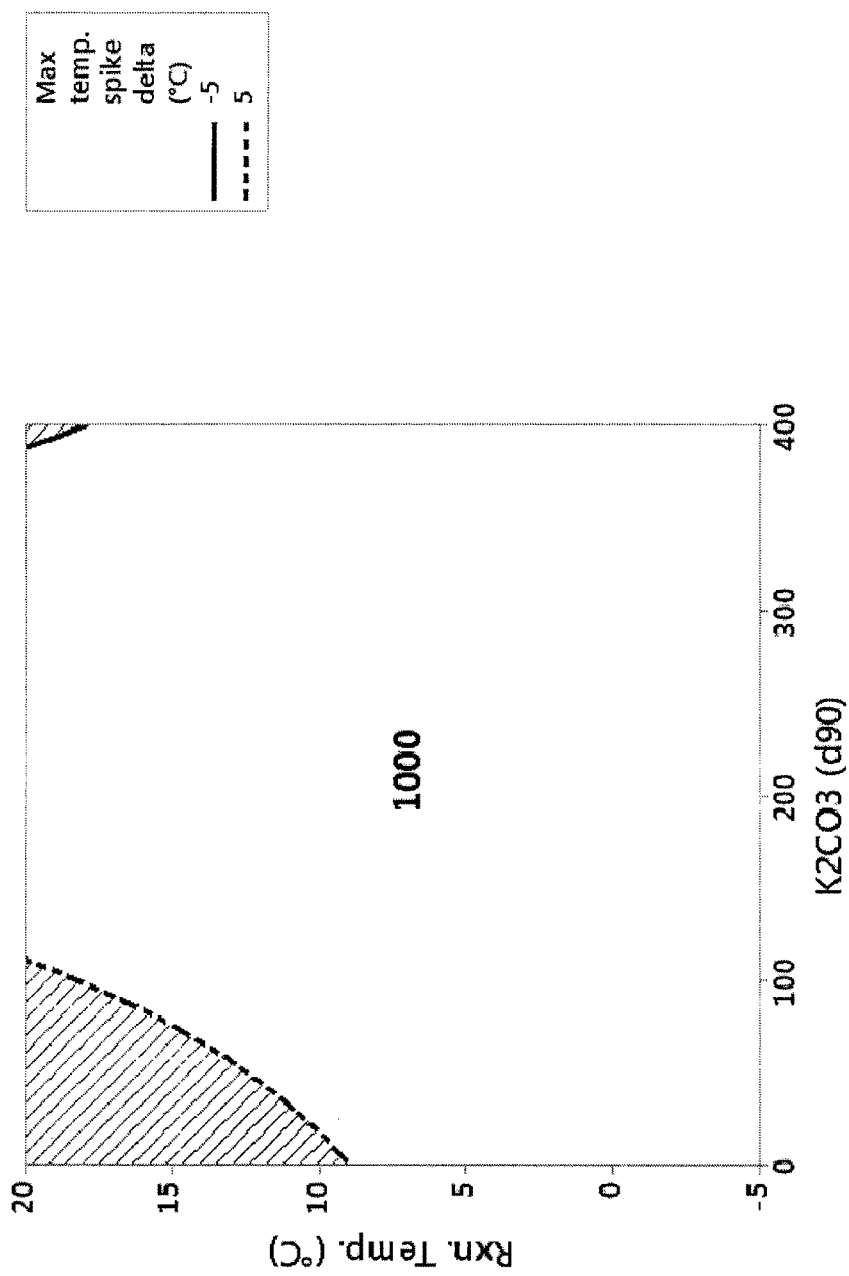

FIG. 10 is the contour plot of temperature spike after potassium carbonate charge versus potassium carbonate particle size and reaction temperature. Y-axis shows the maximum reaction temperature spike in degrees Celsius ("Rxn. Temp. (° C.)"); x-axis shows the D90 values of potassium carbonate in micrometers ("K2CO3 (d90)"). Shaded area to the right of the solid line shows reaction conditions that correspond to a larger than 5° C. decrease in temperature upon potassium carbonate charge; shaded area to the left of the dashed line shows reaction conditions that correspond to a larger than 5° C. increase in temperature upon potassium carbonate charge.

Figure 11:
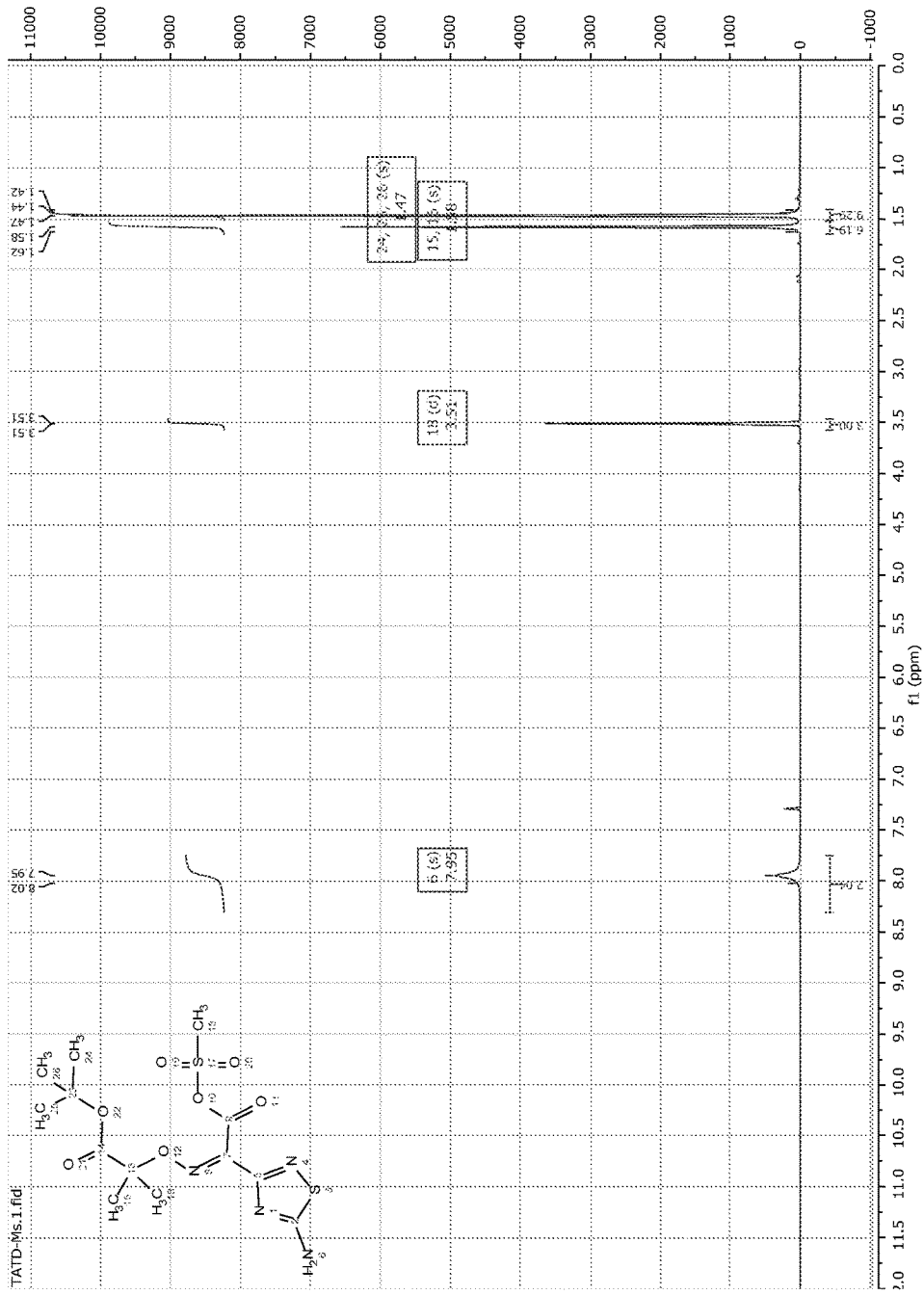

FIG. 11 is the $^1$HT-nuclear magnetic resonance (NMR) spectrum of TATD-Ms (compound (Ib)). Values are in 5 ppm relative to CDCl$_3$ standard (δ 7.26 ppm).

Figure 12:
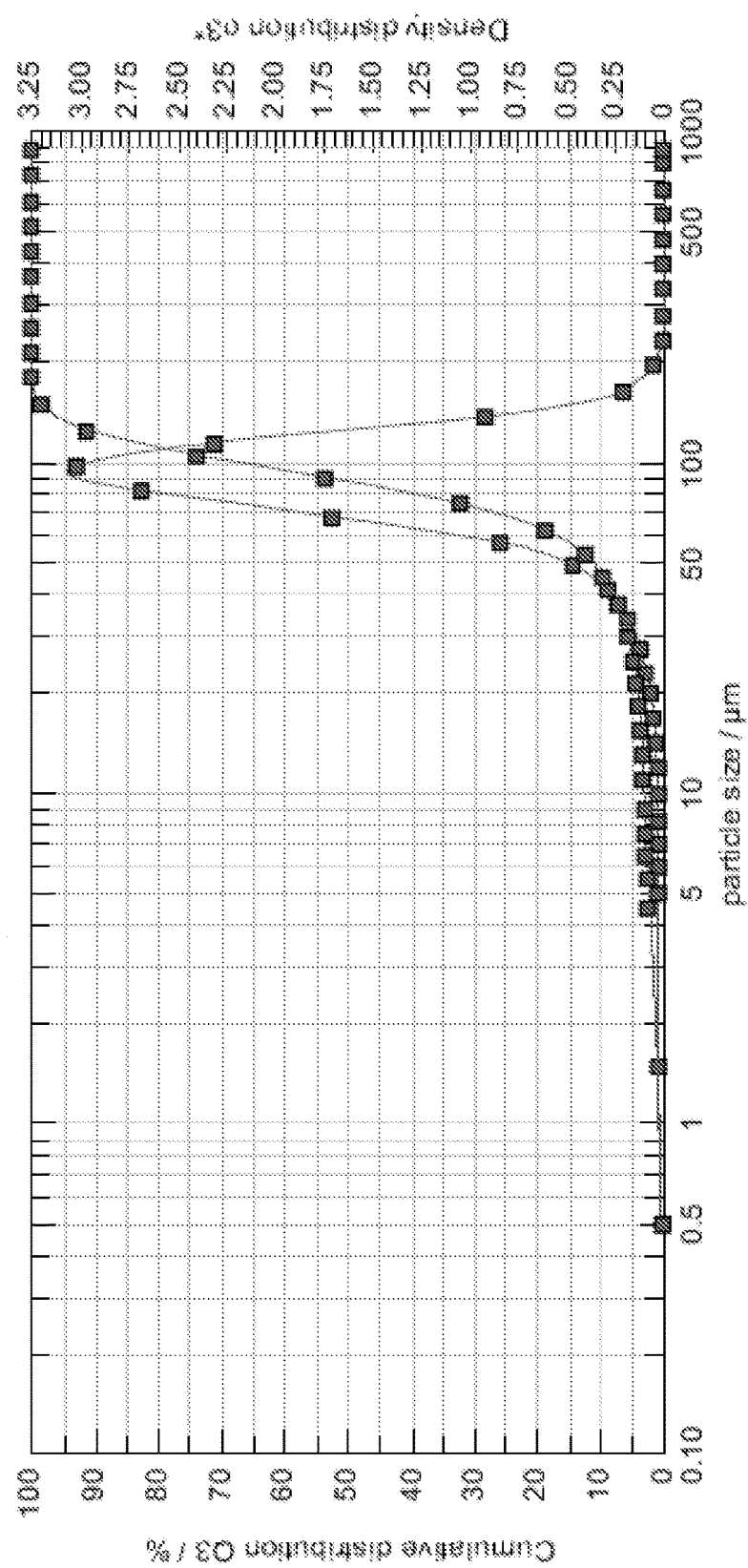

FIG. 12 shows an exemplary particle size distribution of a sample of potassium carbonate of 170-200 mesh size.

X-axis shows particle size in micrometers; left y-axis shows percent cumulative distribution; right y-axis shows density distribution.

6. DETAILED DESCRIPTION

6.1. Definitions

As used herein, the term D90 refers to the $D_i90$ (where "i" refers to the intensity, as obtained on Sympatec HELOS (H1914) using RODOS dispersion system). D90 is defined as the size value corresponding to the cumulative size distribution at 90%, which represents the size of particles below which 90% of the sample lies.

As used herein, the term mesh size refers to,

| Mesh Size | Size in (mm) |
| --- | --- |
| 35 mesh | 0.500 mm |
| 80 mesh | 0.180 mm |
| 100 mesh | 0.150 mm |
| 120 mesh | 0.125 mm |
| 140 mesh | 0.106 mm |
| 170 mesh | 0.090 mm |
| 200 mesh | 0.0750 mm |
| 230 mesh | 0.0630 mm |
| 270 mesh | 0.0530 mm |
| 325 mesh | 0.0450 mm |
| 400 mesh | 0.0374 mm |

Mesh size refers to a sieve analysis of particle size where, e.g., the particles have been filtered through a wire mesh of a certain size. An appropriate selection of wire mesh sizes can provide the range of particle sizes as disclosed herein. In an illustrative example, a sample having particles of 170 mesh size or higher can be generated by filtering through a wire mesh having square holes 0.090 mm in size. In another example, a sample having particles of 200-400 mesh size can be made by filtering through a wire mesh with square holes of 0.0750 mm in size (i.e., 200 mesh), then taking the filtered material and removing smaller particles by filtering the material through a wire mesh with square holes of 0.0374 mm in size (i.e., 400 mesh).

As used herein, the term compound (I) refers to a compound of formula (I); the term compound (Ib) refers to a compound of formula (Ib); and the term compound (III) refers to a compound of formula (III).

6.2. General Synthetic Route

Figure 1A:
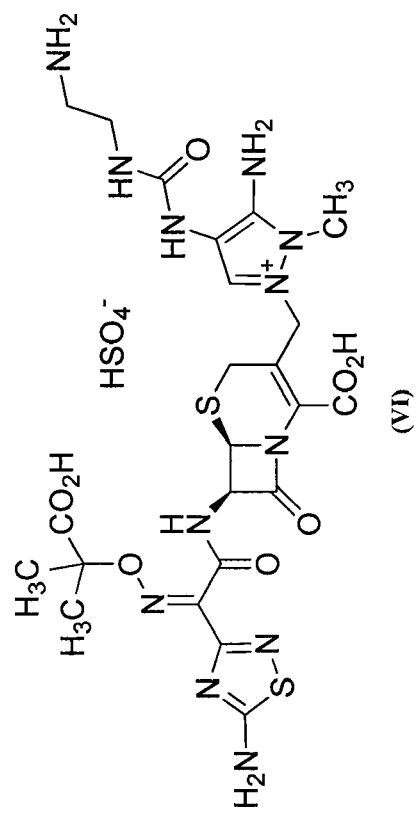
FIG. 1A is the chemical structure of ceftolozane sulfate.
Figure 1B:
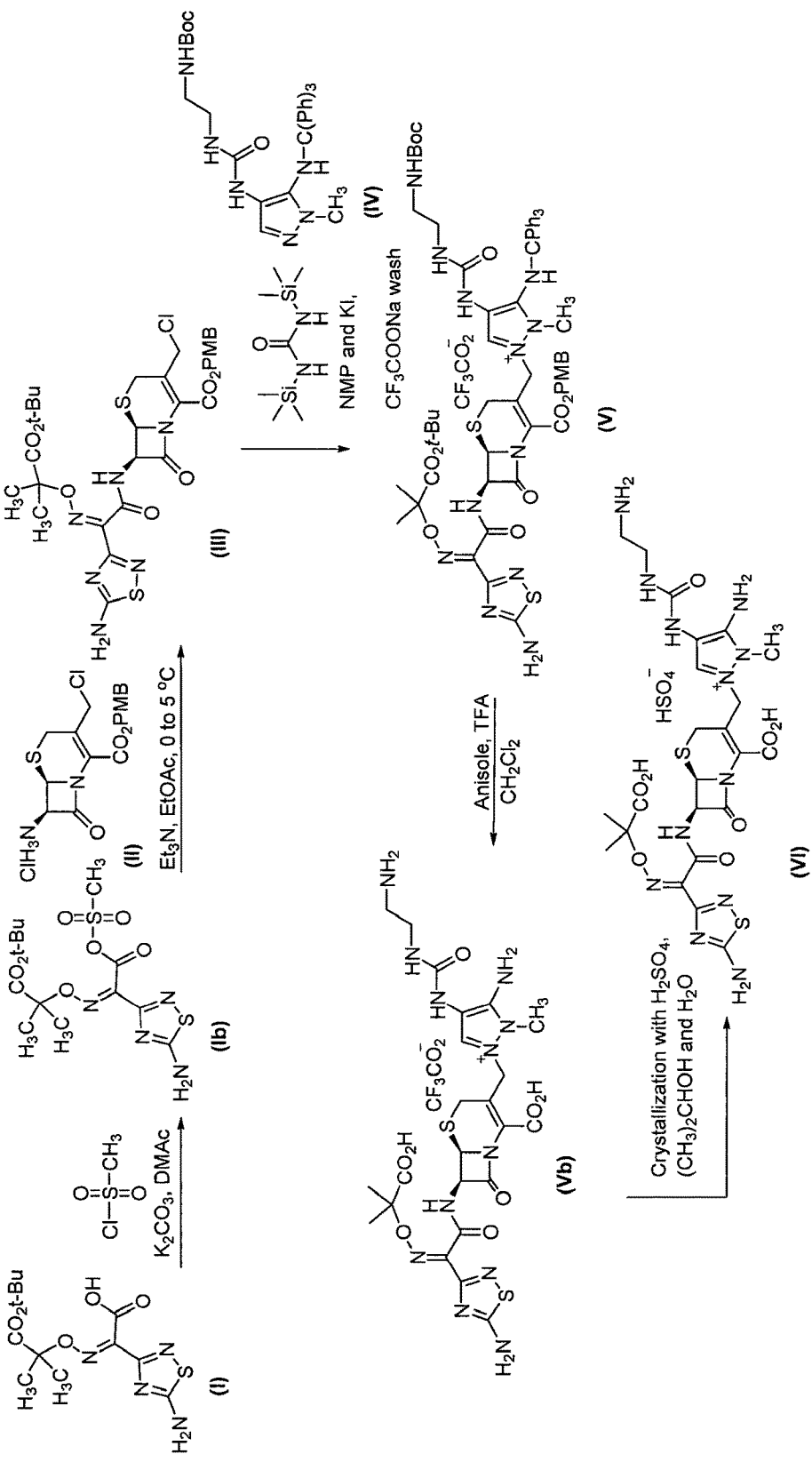
FIG. 1B is a synthetic scheme for preparing ceftolozane sulfate from starting material TATD (compound (I)).
Figure 1C:
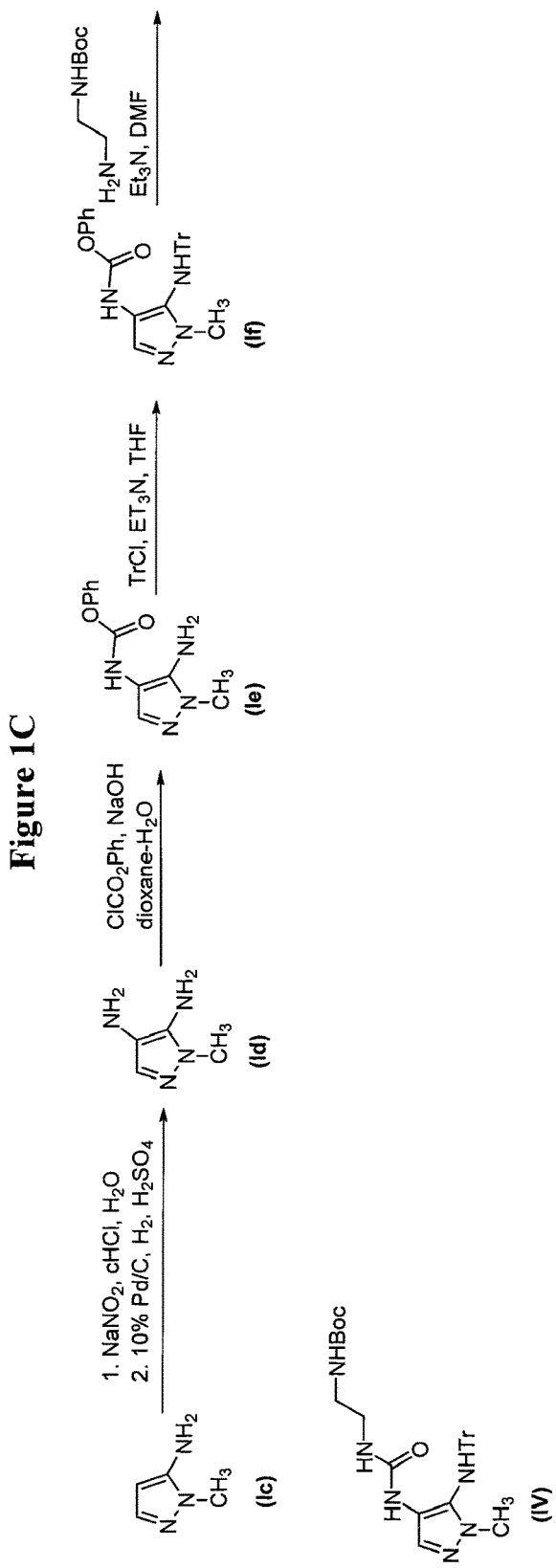
FIG. 1C is a synthetic scheme for preparing starting material 5-amino-1-methylpyrazole, which is used in the manufacturing of ceftolozane sulfate as disclosed in *Bioorganic & Medicinal Chemistry Letters*, 18, 4849-4852 (2008).
Figure 1D:
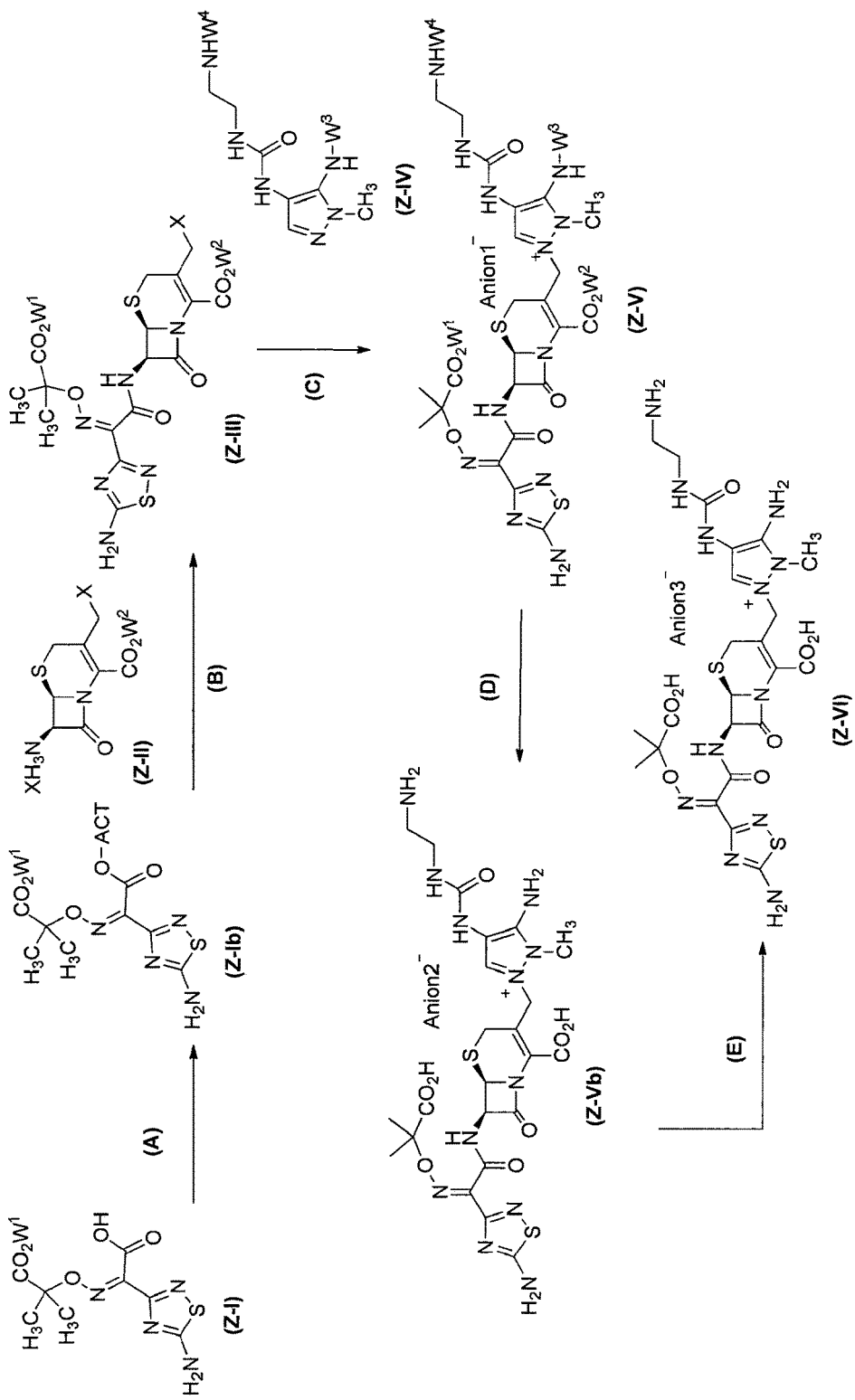
FIG. 1D is a general synthetic route to a salt of ceftolozane.

In certain aspects, the present disclosure provides improved methods of making one or more compounds shown in the general synthetic route described in FIG. 1D.

As used herein, $W^1$ is an ester protecting group. In some embodiments, $W^1$ is a $C_1$-$C_6$ alkyl, such as Me, Et, or tert-butyl. In some embodiments, $W^1$ is a base-labile protecting group (i.e., one that is removed under basic conditions), such as but not limited to Me, Et, and propyl. In some embodiments, W' is a protecting group that can be removed under hydrogenation conditions, such as benzyl. In some embodiments, $W^1$ is an acid-labile protecting group (i.e., one that is removed under acid conditions), such as but not limited to tert-butyl, para-methoxybenzyl, ortho-methoxybenzyl, or diphenylmethyl, preferably tert-butyl.

As used herein, a "$C_x$-$C_y$" group is a group having a number of carbons between x and y, inclusive. For example, a $C_1$-$C_6$ alkyl is an unsubstituted alkyl having one to six carbons, e.g., methyl (Me), ethyl (Et), or tert-butyl.

As used herein, $W^2$ is an ester protecting group. In some embodiments, $W^2$ is a protecting group that is removed under acid conditions, such as but not limited to tert-butyl, para-methoxybenzyl, ortho-methoxybenzyl, or diphenylmethyl, preferably para-methoxybenzyl.

As used herein, X is a halide, such as Cl, Br, or I, preferably Cl.

As used herein, $W^3$ is an amine protecting group. In some embodiments, $W^3$ is selected from triphenylmethyl, tert-butyl, tert-butoxycarbonyl, and para-methoxybenzoyl, preferably triphenylmethyl.

As used herein, $W^4$ is an amine protecting group. In some embodiments, $W^4$ is selected from triphenylmethyl, tert-butyl, tert-butoxycarbonyl, and para-methoxybenzoyl, preferably tert-butoxycarbonyl.

As used herein, Anion1, Anion2, and Anion3 is each independently a pharmaceutically acceptable salt. In some embodiments, Anion1, Anion2, and Anion3 is each independently selected from halide (e.g., chloride, bromide, or iodide), trifluoroacetate, trifluoromethanesulfonate, methanesulfonate, toluenesulfonate, hydrogen sulfate, and sulfate. In some embodiments, two or more of Anion1, Anion2, and Anion3 are the same. In some embodiments, Anion1, Anion2, and Anion3 are all different. In some embodiments, Anion1 is trifluoroacetate. In some embodiments, Anion2 is trifluoroacetate. In some embodiments, Anion3 is hydrogen sulfate.

It should be noted that $W^1$, $W^2$, $W^3$, $W^4$, $R^S$, X, Anion1, Anion2, and Anion3 are consistent throughout the synthetic sequence defined in FIG. 1D. For example, when W' is tert-butyl in a compound of formula (Z-I), then all subsequent compounds, e.g., a compound of formula (Z-Ib-1) or a compound of formula (Z-III), have W'=tert-butyl.

A compound of formula (Z-I) can be obtained by methods known in the art, for example, in U.S. Pat. No. 7,129,232. In some embodiments, a compound of formula (Z-I) is compound (I).

A compound of formula (Z-I) can be converted to the activated carbonyl compound of formula (Z-Ib) by treatment under Conditions (A). The activating group -ACT can be any activating group. In some embodiments, -ACT is a halide, e.g., —F, —Cl, or —Br. Conditions (A) can comprise agents that convert a carboxylic acid to a carboxylic acid halide, e.g., $POCl_3$ to form an acid chloride.

In some embodiments, -ACT is —$OSO_2R^S$, wherein $R^S$ is a $C_1$-$C_6$ alkyl, e.g., Me or Et, or a substituted or unsubstituted phenyl. When -ACT is —$OSO_2R^S$, the conversion of a compound of formula (Z-I) to a compound of formula (Z-Ib) can occur with treatment with a compound of formula $R^SSO_2X^1$, wherein $X^1$ is a halide such as Cl, Br, or I. In some embodiments, -ACT is an activated ester, e.g., methanesulfonate (—OMs), toluenesulfonate (—OTs), trifluoromethanesulfonate (—OTf), or pentafluorophenyl ester. In some embodiments, -ACT is a mixed anhydride, e.g., —O(C=O)$R^A$, where $R^A$ is a $C_1$-$C_6$ alkyl (for example, Me or Et) or a substituted or unsubstituted $C_6$-$C_{10}$ aryl group (for example, phenyl; 1,3,6-trichlorophenyl; or naphthyl). In certain embodiments, -ACT is —OMs.

In some embodiments, the compound of formula (Z-Ib) has the structure of formula (Z-Ib-1):

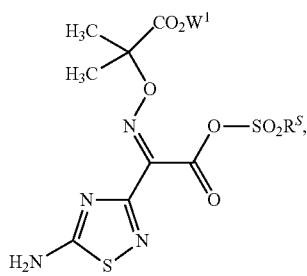

(Z-Ib-1)

wherein $W^1$ and $R^S$ are as defined herein.

In some embodiments, the compound of formula (Z-Ib) is compound (Ib).

In one aspect, the compound of formula (Z-Ib), e.g., a compound of formula (Ib), is synthesized in high yield and/or high purity. In some embodiments, the compound of formula (Z-Ib) is synthesized in at least about 80%, such as at least about 85%, at least about 90%, at least about 95%, at least about 97%, or at least about 99% yield.

In some embodiments, the compound of formula (Z-Ib), e.g., a compound of formula (Ib), is substantially pure, for example, with purity levels of at least about 80%, such as at least about 85%, at least about 90%, at least about 95%, at least about 97%, or at least about 99%. In some embodiments, the purity is determined by methods known in the art, such as NMR spectroscopy, e.g., $^1H$ or $^{13}C$ NMR.

In some embodiments, Conditions (A) comprise a methanesulfonyl halide, e.g., chloride or bromide; a base, e.g., an organic base such as triethylamine or diisopropylethylamine, or an inorganic base such as an alkali metal carbonate, e.g., lithium carbonate, sodium carbonate, or potassium carbonate; and an appropriate solvent. In some embodiments, Conditions (A) comprise methanesulfonyl chloride. In some embodiments, Conditions (A) comprise potassium carbonate. In some embodiments, Conditions (A) comprise a solvent selected from ethyl acetate, isopropyl acetate, tetrahydrofuran, methyl tert-butyl ether, dimethylformamide, and dimethylacetamide, preferably dimethylacetamide.

The activated compound of formula (Z-Ib) can react with a compound of formula (Z-II) under Conditions (B) to provide an amide compound of formula (Z-III). In some embodiments, the compound of formula (Z-Ib) is combined with a compound of formula (Z-II) in an appropriate solvent in the presence of a base in an appropriate solvent to give a compound of formula (Z-III). In some embodiments, Conditions (B) comprise an organic base, such as triethylamine, diethylamine, or diisopropylethylamine. In some embodiments, Conditions (B) comprise triethylamine. In some embodiments, Conditions (B) comprise a solvent selected from ethyl acetate, isopropyl acetate, tetrahydrofuran, methyl tert-butyl ether, dimethylformamide, and dimethylacetamide. In some embodiments, Conditions (B) comprise ethyl acetate. In some embodiments, a compound of formula (Z-II) is a compound of formula (II). In some embodiments, a compound of formula (Z-III) is compound (III).

In one aspect, the compound of formula (Z-III), e.g., a compound of formula (III), is synthesized in high yield and/or high purity. In some embodiments, the compound of formula (Z-III) is synthesized in at least about 80%, such as at least about 85%, at least about 90%, at least about 95%, at least about 97%, or at least about 99% yield.

The compound of formula (Z-III) can undergo displacement by a compound of formula (Z-IV) to afford a compound of formula (Z-V). Conditions (C) can comprise any method that allows for displacement of an allylic halide by an aromatic amine. In some embodiments, Conditions (C) comprise a polar aprotic solvent such as tetrahydrofuran, dimethylformamide (also known as N, N-dimethylformamide or DMF), dimethylacetamide (also known as N, N-dimethylacetamide or DMAc), and N-methylpyrrolidone (NMP). For example, Conditions (C) can comprise NMP. In some embodiments, a compound of formula (Z-IV) is a compound of formula (IV). In some embodiments, a compound of formula (Z-V) is a compound of formula (V).

In one aspect, the compound of formula (Z-V), e.g., a compound of formula (V), is synthesized in high yield and/or high purity. In some embodiments, the compound of formula (Z-V) is synthesized in at least about 80%, such as at least about 85%, at least about 90%, at least about 95%, at least about 97%, or at least about 99% yield.

In some embodiments, Conditions (C) comprise reagents that contribute to a higher yield and/or a cleaner reaction. In some embodiments, Conditions (C) comprise potassium iodide. In some embodiments, Conditions (C) comprise N, N'-bis(trimethylsilyl)urea.

A compound of formula (Z-V) can be deprotected under Conditions (D) to provide a compound of formula (Z-Vb). In some embodiments, one or more of $W^1$, $W^2$, $W^3$, and $W^4$ is removed under Conditions (D) comprising an acid. In some embodiments, Conditions (D) comprise an acid selected from one or more of: trifluoroacetic acid, trifluoromethanesulfonic acid, methanesulfonic acid, toluenesulfonic acid, sulfuric acid, hydrochloric acid, and hydrobromic acid. In some embodiments, Conditions (D) comprise trifluoroacetic acid. In some embodiments, a compound of formula (Z-Vb) is a compound of formula (Vb).

A compound of formula (Z-Vb) can optionally undergo salt exchange under Conditions (E) to afford a compound of formula (Z-VI). In some embodiments, one salt form, e.g., hydrogen sulfate, is preferred over another salt form, e.g., trifluoroacetate, for a variety of reasons, such as but not limited to crystallinity, solubility, hygroscopicity, and/or filterability. In some embodiments, Conditions (E) comprise treatment with an excess of the acid of Anion3. In some embodiments, a compound of formula (Z-VI) is a compound of formula (VI).

In one aspect, the compound of formula (Z-VI), e.g., a compound of formula (VI), is synthesized in high yield and/or high purity. In some embodiments, the compound of formula (Z-VI) is synthesized in at least about 80%, such as at least about 85%, at least about 90%, at least about 95%, at least about 97%, or at least about 99% yield.

6.3. Compound (Ib) from Compound (I)

In some aspects, the ceftolozane synthetic methods as referenced herein are based on optimizing the synthesis of the intermediates or changing the order of the reactants or intermediates added during the reaction. This can include, for example, activation of a thiadiazolyl-oximinoacetic acid, e.g., a compound of formula (Z-I), e.g., compound (I), with phosphoryl chloride in a conventional solvent such as N, N-dimethylformamide to obtain an acid halide compound, which is further reacted with an 7-aminocephem compound, e.g., a compound of formula (Z-II), e.g., compound (II), followed by a series of subsequent reactions to obtain a cephalosporin, e.g., a compound of formula (Z-VI), e.g., a compound of formula (VI), e.g., ceftolozane sulfate (see, e.g., U.S. Pat. No. 7,129,232). As disclosed in U.S. Pat. No. 7,192,943, activation of the thiadiazolyl-oximinoacetic acid (compound (I)) can also be carried out with methanesulfonyl chloride in a conventional solvent such as N, N-dimethylacetamide to obtain a acid halide compound, which is further reacted with 7-aminocephem compound (II) followed by series of reactions to obtain ceftolozane sulfate (a compound of formula (VI)).

In some embodiments, the methods disclosed herein provide a desirably high yield of the conversion of a compound of formula (Z-I), e.g., compound (I), into a compound of formula (Z-Ib), e.g., compound (Ib), and increase the yield of the intermediates such as a compound of formula (Z-III), e.g., compound (III), which can be used in the subsequent steps to manufacture a compound of formula (Z-VI), e.g., ceftolozane sulfate (a compound of formula (VI)). Higher yield processes can reduce manufacturing costs associated with, for example, the exemplary starting material TATD compound (I), which can be commercially obtained as [(Z)-2-(5-amino-1,2,4-thiadiazol-3-yl)-2-(((1-(tert-butoxy)-2-methyl-1-oxopropan-2-yl)oxy)imino) acetic acid], (CAS 76028-96-1). Compound (I) is a valuable starting material used during the manufacturing of ceftolozane sulfate, so it is desirable to identify synthetic processes that utilize lower equivalents of compound (I); however, greater guidance is needed to improve the yield of certain intermediates in the manufacture of ceftolozane. For example, one step of the process comprises synthesizing compound (III) by reacting compound (II) with compound (Ib), which is obtained via the activation of compound (I).

Methods for converting a compound of Formula (I) to a compound of Formula (Ib) with desirably high yields (e.g., at least about 90%) are disclosed herein. TATD-Ms (compound (Ib)) can be prepared from [(Z)-2-(5-amino-1,2,4-thiadiazol-3-yl)-2-(((1-(tert-butoxy)-2-methyl-1-oxopropan-2-yl)oxy)imino) acetic acid] (CAS 76028-96-1). The compound of Formula (Ib) is provided below, also called TATD-Ms

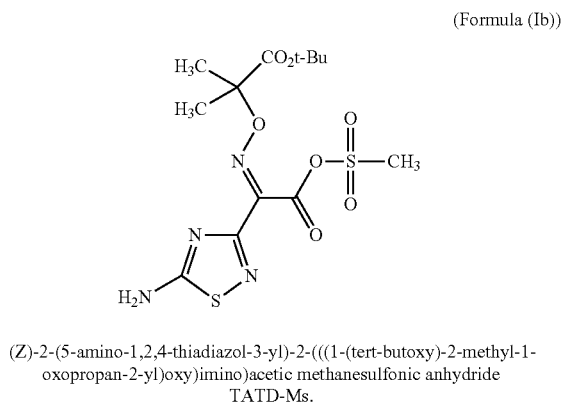

(Z)-2-(5-amino-1,2,4-thiadiazol-3-yl)-2-(((1-(tert-butoxy)-2-methyl-1-oxopropan-2-yl)oxy)imino)acetic methanesulfonic anhydride TATD-Ms.

Figure 2:
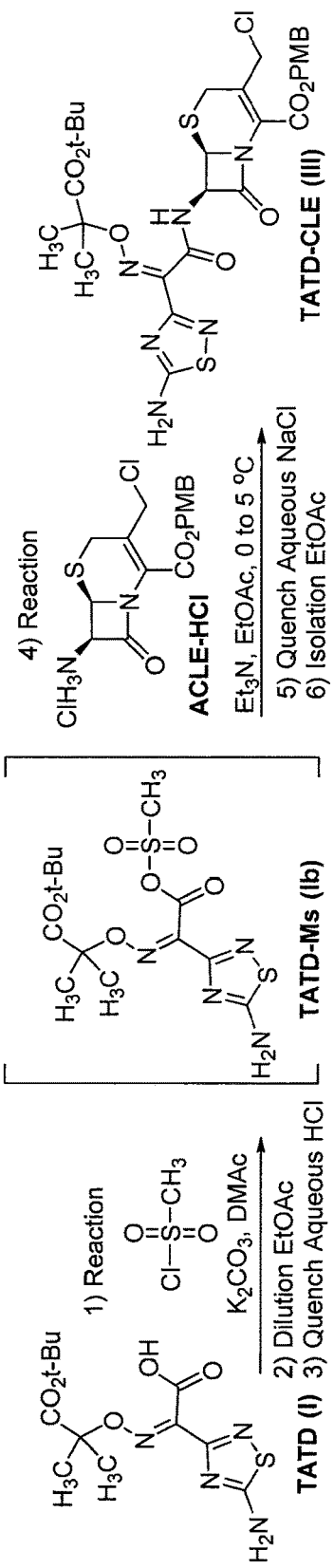
FIG. 2 is a synthetic scheme for preparing ceftolozane drug intermediate TATD-CLE (compound (III)) from TATD-Ms (compound (Ib)) via activation of starting material TATD (compound (I)).

TATD (compound (I)) can be converted to TATD-Ms (compound (Ib)) via the reaction scheme shown in FIG. 2, and TATD-Ms can be used in the manufacturing of novel cephalosporin such as ceftolozane (compound (VI)). For example, one process disclosed herein comprises conversion of TATD to TATD-Ms with methanesulfonyl chloride in the presence of 1.05 to 1.30 equivalents of potassium carbonate particles having a D90 of 70-250 micrometers (i.e., 90% of the particles has a size within a range of from 70 to 250 micrometers), effective to provide 90% of conversion of compound (I) to compound (Ib).

In some embodiments, a compound of formula (Z-Ib), e.g., compound (Ib), is obtained in at least about 80% purity, such as at least about 85%, at least about 90%, at least about 95%, at least about 97% or at least about 99% purity.

In some embodiments, the yield of a compound of formula (Z-Ib), e.g., compound (Ib), from a compound of formula (Z-I), e.g., compound (I), is at least about 80%, such as at least about 85%, at least about 90%, at least about 95%, at least about 97% or at least about 99%.

The present disclosure also includes the reaction of compound (I) that is carried out within about 3 hours of reaction time in solution, preferably in a solvent such as DMAc [N,N-dimethylacetamide], at a temperature of about 0-10 degrees C. to obtain at least 90% conversion of compound (I) to compound (Ib). Compound (Ib) in FIG. 2, or a salt thereof, can be prepared by reacting compound (I), or a salt thereof, with methanesulfonyl chloride. The reaction can be carried out in a suitable polar organic solvent such as DMAc [N, N-dimethylacetamide], DMF [N, N-dimethylformamide], or NMP [N-methylpyrrolidinone]. In certain embodiments, the polar organic solvent is DMAc. The reaction can be performed in an anhydrous solvent so as to improve product yield and avoid or minimize degradation of the product. In this reaction, when the compound (I) is used in free acid form or its salt form, the reaction is preferably carried out in the presence of a base, for example, an inorganic base such as alkali metal carbonate like lithium carbonate, sodium carbonate, or potassium carbonate, preferably potassium carbonate. Reaction conditions such as (but not limited to) molar ratio of reactants TATD, methanesulfonyl chloride, potassium carbonate, particle size of potassium carbonate, reaction temperature conditions and total reaction time can be selected as disclosed herein to obtain improved yield, for example at least 90% conversion of compound of formula (I) to compound of formula (Ib) or salt thereof.

FIG. 3 is a data table showing data obtained from running the reaction scheme in FIG. 2 under different parameters. As disclosed herein, six different reaction parameters were varied in a series of 20 different reactions of conversion of compound (I) to compound (Ib) according to the reaction scheme shown in FIG. 2. The six selected parameters selected were: equivalent ratios (stoichiometry) of TATD (I), methanesulfonyl chloride, and potassium carbonate; mesh size of potassium carbonate particles; D90 of potassium carbonate particles; and reaction temperature. The effect of these six selected parameters on the conversion of compound (I) to compound (Ib) was observed for up to 3 hours.

An exemplary particle distribution profile of a sample of potassium carbonate as determined by a Sympatec HELOS laser diffraction sensor is shown in FIG. 12. The sample of potassium carbonate has a normal size distribution with a large number of particles centered around about 80-100 micrometers. $D_{10}$=47 micrometers (i.e., 10% of the particles by weight is less than 47 micrometers in size); $D_{50}$=87.7 micrometers (i.e., 50% of the particles by weight is less than 87.7 micrometers in size); $D_{90}$=124 micrometers (i.e., 90% of the particles by weight is less than 124 micrometers in size).

As used herein, "μm" or micrometers are used interchangeably, and refer to $10^{-6}$ meters in a linear dimension.

In one aspect, particle size of the potassium carbonate can be selected by using potassium carbonate of mesh size such as, but not limited to, <400, 120-200, or 35-80 mesh sizes as disclosed herein.

The mesh size can be used to obtain the size of 90% (D90) potassium carbonate particles by a particle size analyzer for example, but not limited to, 27 μm, 228 μm, and 497 μm.

In some embodiments, the alkali metal carbonate, e.g., potassium carbonate, particles have at least about 50%, at least about 60%, at least about 70%, at least about 80%, or at least about 90%, preferably at least about 90%, of the particles by weight within a range of from about 20 to about 500 μm, such as from about 20 to about 480 μm, about 20 to about 400 μm, about 20 to about 360 μm, about 20 to 300 μm, about 20 to 250 μm, about 20 to about 200 μm, about 20 to about 160 μm, about 20 to about 100 μm, or about 20 to about 60 μm; such as from about 70 to about 480 μm, such as from about 70 to about 460 μm, about 70 to about 400 μm, about 70 to about 360 μm, about 70 to about 300 μm, about 70 to about 250 μm, about 70 to about 200 μm, about 70 to about 180 μm, about 70 to about 140 μm, about 70 to about 120 μm; such as from about 100 to about 480 μm, about 100 to about 400 μm, about 100 to about 360 μm, about 100 to about 300 μm, about 100 to about 250 μm, about 100 to about 200 μm, about 100 to about 160 μm; such as from about 140 to about 480 μm, such as from about 140 to about 440 μm, about 140 to about 400 μm, about 140 to about 360 μm, about 140 to about 300 μm, about 140 to about 250 μm, about 140 to about 200 μm; such as from about 200 to about 480 μm, about 200 to about 400 μm, about 200 to about 360 μm, about 200 to about 300 μm, about 200 to about 280 μm, about 200 to about 250 μm; such as from about 300 to about 480 μm, such as from about 300 to about 460 μm, about 300 to about 400 μm, or about 300 to about 340 μm; or such as from about 400 to about 480 μm.

As used herein, when D90 is referred to as within a range, it refers to the size range at which at least about 90% of the particles by weight of the sample falls. In an illustrative example, a D90 of about 70 to about 180 μm means at least about 90% of the particles by weight falls in a size range from about 70 to about 180 μm.

The reaction can be performed in improved yield when the mesh size of potassium carbonate particles is 120-200, whereas using potassium carbonate particles of mesh size, but not limited to, <400 or 35-80 can result in reaction mixture that is very viscous and difficult to agitate.

Referring to the data in FIG. 3, when the molar equivalent ratio of TATD (compound (I)) is 0.9 (see, for example, samples 1-4 and 13-16), or when the molar equivalent ratio is 1.3 (see, for example, samples 5-8 and 17-20), the reaction mixture was determined to be undesirably viscous and difficult to agitate. (In FIGS. 3 and 4, the molar equivalents of TATD, MsCl, and potassium carbonate are relative to the amount of compound (II) (1.0 equivalent) used in the two-step process of converting compound (I) to compound (III).) Under these conditions, the reaction stalls, affording poor yields of TATD-Ms (compound (Ib)). However, when the molar equivalent ratio of TATD is 1.1 (see, for example, samples 9-12, in FIG. 3), the desired product (i.e., compound (Ib)) was obtained in improved yield with high purity, such as greater than about 90%, e.g., about 95%, about 97%, or about 99%.

In some embodiments, the molar equivalent ratio of a compound of formula (Z-I), e.g., TATD, to a compound of formula (Z-II), e.g., compound (II), is in a range of from about 1.0 to about 1.4, such as about 1.1 to about 1.3, about 1.2 to about 1.4, or about 1.0 to about 1.2. In some embodiments, the molar equivalent ratio of the compound of formula (Z-I) is about 1.0, about 1.1, about 1.2, about 1.3, or about 1.4, preferably about 1.1.

In some embodiments, the molar equivalent ratio of the compound of formula (Z-I), e.g., TATD, to an alkali metal carbonate, e.g., potassium carbonate, is in a range of from about 0.6 to about 1.4, such as from about 0.7 to about 1.4, about 0.8 to about 1.4, about 0.9 to about 1.4, about 1.0 to about 1.4, about 1.1 to about 1.4; such as from about 0.6 to about 1.3, about 0.7 to about 1.3, about 0.8 to about 1.3, about 0.9 to about 1.3, about 1.0 to about 1.3, about 1.1 to about 1.3; or such as from about 0.6 to about 1.2, about 0.7 to about 1.2, about 0.8 to about 1.2, about 0.9 to about 1.2, about 1.0 to about 1.2. In some embodiments, the molar equivalent ratio of the compound of formula (Z-I) to potassium carbonate is about 0.6, about 0.7, about 0.8, about 0.9, about 1.0, about 1.1, about 1.2, about 1.3, or about 1.4.

In some embodiments, the molar equivalent ratio of a compound of formula $R^SSO_2X^1$, e.g., wherein $R^S$ is Me and $X^1$ is Cl (i.e., methanesulfonyl chloride), to the compound of formula (Z-I), e.g., TATD, is in a range of from about 1.0 to about 3.0, such as about 1.0 to about 2.8, about 1.0 to about 2.6, about 1.0 to about 2.4, about 1.0 to about 2.2, about 1.0 to about 2.0, about 1.0 to about 1.8, about 1.0 to about 1.6, about 1.0 to about 1.4, or about 1.0 to about 1.2; such as 1.3 to about 3.0, such as about 1.3 to about 2.8, about 1.3 to about 2.6, about 1.3 to about 2.4, about 1.3 to about 2.2, about 1.3 to about 2.0, about 1.3 to about 1.8, about 1.3 to about 1.6; such as about 1.6 to about 3.0, such as about 1.6 to about 2.8, about 1.6 to about 2.6, about 1.6 to about 2.4, about 1.6 to about 2.2, about 1.6 to about 2.0, or about 1.6 to about 1.8; such as about 1.8 to about 3.0, such as about 1.8 to about 2.8, about 1.8 to about 2.6, about 1.8 to about 2.4, about 1.8 to about 2.2, or about 1.8 to about 2.0; such as about 2.0 to about 3.0, such as about 2.0 to about 2.8, about 2.0 to about 2.6, about 2.0 to about 2.4, or about 2.0 to about 2.2; such as about 2.2 to about 3.0, such as about 2.2 to about 2.8, about 2.2 to about 2.6, or about 2.2 to about 2.4; such as about 2.4 to about 3.0, such as about 2.4 to about 2.8, or about 2.4 to about 2.6; such as about 2.6 to about 3.0, or about 2.6 to about 2.8.

In some embodiments, the molar equivalent ratio of a compound of formula $R^SSO_2X^1$, e.g., methanesulfonyl chloride, to the compound of formula (Z-I), e.g., TATD, is about 1.0, about 1.2, about 1.3, about 1.4, about 1.6, about 1.8, about 2.0, about 2.2, about 2.4, about 2.6, about 2.8, or about 3.0.

In some embodiments, the molar equivalent ratio of a compound of formula $R^SSO_2X^1$, e.g., methanesulfonyl chloride, to an alkali metal carbonate, e.g., potassium carbonate, is in a range of about 1.0 to about 3.0, such as about 1.0 to about 2.8, about 1.0 to about 2.6, about 1.0 to about 2.4, about 1.0 to about 2.2, about 1.0 to about 2.0, about 1.0 to about 1.8, about 1.0 to about 1.6, about 1.0 to about 1.4, or about 1.0 to about 1.2; such as 1.3 to about 3.0, such as about 1.3 to about 2.8, about 1.3 to about 2.6, about 1.3 to about 2.4, about 1.3 to about 2.2, about 1.3 to about 2.0, about 1.3 to about 1.8, about 1.3 to about 1.6; such as about 1.6 to about 3.0, such as about 1.6 to about 2.8, about 1.6 to about 2.6, about 1.6 to about 2.4, about 1.6 to about 2.2, about 1.6 to about 2.0, or about 1.6 to about 1.8; such as about 1.8 to about 3.0, such as about 1.8 to about 2.8, about 1.8 to about 2.6, about 1.8 to about 2.4, about 1.8 to about 2.2, or about 1.8 to about 2.0; such as about 2.0 to about 3.0, such as about 2.0 to about 2.8, about 2.0 to about 2.6, about 2.0 to about 2.4, or about 2.0 to about 2.2; such as about 2.2 to about 3.0, such as about 2.2 to about 2.8, about 2.2 to about 2.6, or about 2.2 to about 2.4; such as about 2.4 to about 3.0, about 2.4 to about 2.8, or about 2.4 to about 2.6; such as about 2.6 to about 3.0, or about 2.6 to about 2.8.

In some embodiments, the molar equivalent ratio of a compound of formula $R^SSO_2X^1$, e.g., methanesulfonyl chloride, to an alkali metal carbonate, e.g., potassium carbonate, is about 1.0, about 1.2, about 1.3, about 1.4, about 1.6, about 1.8, about 2.0, about 2.2, about 2.4, about 2.6, about 2.8, or about 3.0.

In another aspect, the reaction temperature can be optimized for obtaining improved yield of compound (Ib). For example, the reaction can be carried out at temperature of, 7.5 degrees C. (see, for example, samples 9-12 in FIG. 3). In contrast, reactions carried out at temperature of, for example, −5 degrees C. (see, for example, samples 1, 2, 5, 8, 13, and 16-18 in FIG. 3), or at a reaction temperature of, for example, 20 degrees C. (see, for example, samples 3, 4, 6, 7, 14, 15, 19, and 20 in FIG. 3) can adversely affect the yield of compound (Ib).

As used herein, "° C." or "degrees C." refers to degrees Celsius.

In some embodiments, the reaction temperature is in a range of from about −10 to about 25° C., such as from about −10 to about 20, about −10 to about 15, about −10 to about 10, about −10 to about 5, about −10 to about 0, about −10 to about −5; such as from about −5 to about 25, about −5 to about 20, about −5 to about 15, about −5 to about 10, about −5 to about 5, about −5 to about 0; such as from about 0 to about 25, about 0 to about 20, about 0 to about 15, about 0 to about 10, about 0 to about 5; such as from about 5 to about 25, about 5 to about 20, about 5 to about 15, about 5 to about 10; such as from about 10 to about 25, about 10 to about 20, about 10 to about 15; such as from about 15 to about 25, about 15 to about 20; or such as from about 20 to about 25° C.

In some embodiments, the reaction temperature is about −10, about −7.5, about −5, about 0, about 5, about 7.5, about 10, about 15, about 20, or about 25° C.

In yet another aspect, the reaction time can be optimized to obtain improved yield of compound (Ib). For example, the reaction can be carried out for about 0.5, about 1, or about 1.5 hour. In some embodiments, the reaction time ranges from about 0.5 hour to about 1.5 hours, such as about 0.5 to about 1, about 1 to about 1.5, about 0.5 to about 1.2 hours. In some embodiments, the reaction time is at least about 0.5, at least about 1, or at least about 1.5 hour. In contrast, reactions carried out for longer periods of time, for example, 2 or 3 hours or longer can adversely affect reaction yield. Without being bound by theory, the correlation between longer reaction time and lower reaction yield may be attributed to the decomposition of the resulting product (i.e., compound (Ib)).

Compound (Ib) can be obtained by a method comprising converting at least about 90%, and preferably at least about 97%, of compound (I) to compound (Ib). Suitable ranges of the molar equivalent ratio of the reactants, the particle size of the potassium carbonate, the reaction temperature, and the reaction time than those disclosed herein can be used.

The reaction to obtain compound (Ib) is useful in the manufacture of antibiotics such as cephalosporins, such as ceftolozane (compound (IV)). For example, compound (Ib), or salt thereof, can be reacted with compound (II), or salt thereof, to obtain compound (III), or salt thereof.

FIG. 4 is a data table with additional experimental results from performing the reaction of FIG. 2 under various reaction conditions and parameters. As disclosed herein, six different reaction parameters were varied in 20 reactions involving the conversion of compound (I) to compound (Ib). Six selected parameters were selected: the equivalent ratios of TATD, methanesulfonyl chloride, and potassium carbonate; the mesh size of potassium carbonate particles; the D90 of potassium carbonate particles; and the reaction temperature. The effect of these six parameters on the conversion of compound (I) to compound (Ib) was observed for up to 1.5 hours. The effect of these six parameters on the rise in the temperature of the reaction also was studied.

In one aspect, the particle size of the potassium carbonate can be selected by using potassium carbonate of mesh size such as (but not limited to), 230-270, 170-200 or 80-100. The mesh size can be used to obtain the size of 90% (D90) potassium carbonate particles by particle size analyzer for example but not limited to <230-270=36 µm, 170-200=124 µm and 80-100=249 µm.

The reaction can be performed in improved yield when the mesh size of potassium carbonate particles is (but not limited to) 170-200. In contrast, potassium carbonate particles having a mesh size of, for example, 230-270 or 80-100 can result in a reaction mixture that is very viscous and difficult to agitate.

In another aspect provided herein, a molar equivalent ratio of TATD of, for example, 0.9 (see, for example, samples 4, 6-8, 13, 17, and 18 in FIG. 4) or a molar equivalent ratio of, for example, 1.3 (see, for example, samples 1-3, 5, 14-16, and 19, in FIG. 4) can afford a reaction mixture that is too viscous and difficult to agitate. Under reaction conditions such as these, reaction progress stalls, and poor yields of TATD-Ms (compound (Ib)) can be observed.

In another aspect, a molar equivalent ratio of TATD of, for example, 1.1 (see, for example, samples 9-12, in FIG. 4) can afford the desired product in improved yield and purity as high as 99%.

In another aspect, the reaction temperature can be optimized for obtaining improved yield of compound (Ib). For example, when the reaction is carried out at temperature of 7.5 degrees C., high yields of compound (Ib) are obtained (see, for example, samples 9-12, in FIG. 4). In contrast, reactions carried out at a temperature of, for example, −5 degrees C. (see, for example, samples 1, 4-6, 13-15, and 18, in FIG. 4) or at a temperature of, for example, 20 degrees C. (see, for example, samples 2, 3, 7, 8, 16, 17, 19, and 20, in FIG. 4) demonstrated adverse effects on the yield of compound (Ib).

In yet another aspect, the reaction time can be optimized to obtain improved yield of compound (Ib). For example, the reaction can be carried out for 0.5-1 hours to afford desirable yields of compound (Ib). In contrast, reactions carried out for a time of, for example, 1.5 hours or longer can adversely affect the product yield. Without being bound by theory, the correlation between longer reaction time and lower product yield may be due to decomposition of the product (i.e., compound (Ib)).

Figure 5:
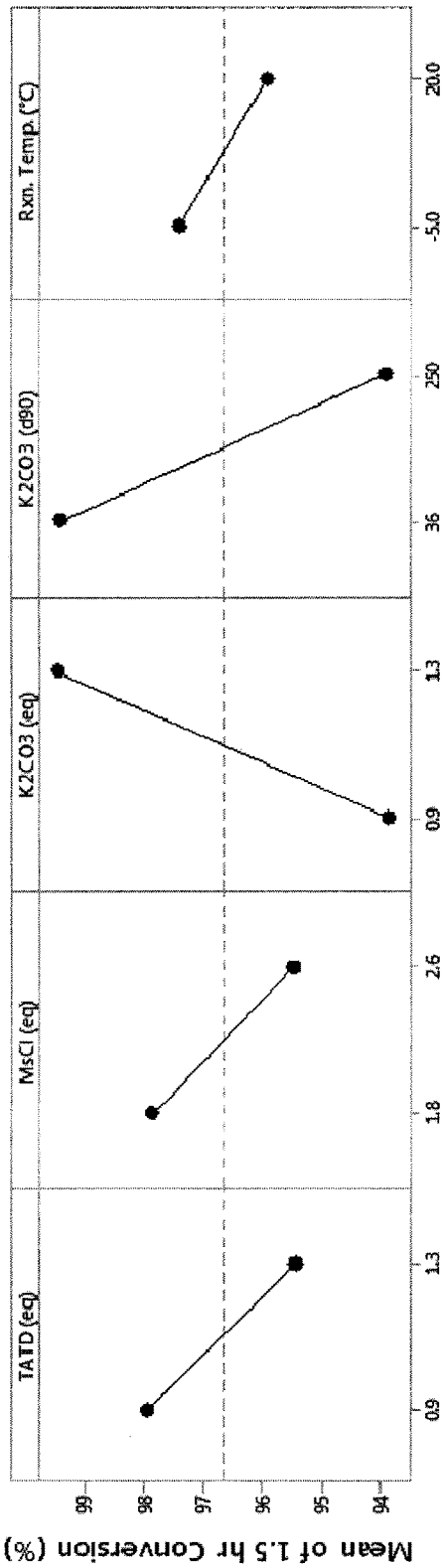
FIG. 5 is the main effects plot for TATD-Ms (compound (Ib)) conversion at 1.5 hours.

FIG. 5 to FIG. 10 are the plots disclosing the effects of the selected parameters on the conversion of compound (I) to compound (Ib) according to the reaction scheme shown in FIG. 2. FIG. 5 is a graph that summarizes the main effects of the reaction parameters. FIG. 6 to FIG. 10 show contour plots of the data generated (from FIG. 4) during the conversion of compound (I) into compound (Ib) by optimizing various selected parameters in a series of 20 different reactions. The data set in FIG. 4 was used to make plots using Minitab17 statistical software. Reaction conversion was plotted against each significant factor identified by the software. All of the five parameters in the study (i.e., molar ratio of reactants TATD, methanesulfonyl chloride, and potassium carbonate; particle size of potassium carbonate; and reaction temperature) and all combinations of these parameters were analyzed for a significant contribution to the reaction conversion. The individual parameters and the various combinations of the parameters that were not significant (i.e., p>0.05) were removed from the model, resulting in the final model shown in the table below.

| Term | Coefficients |
| --- | --- |
| Constant | 129.066 |
| TATD (equiv) | 3.87430 |
| MsCl(equiv) | −12.4699 |
| $K_2CO_3$ (equiv) | −35.5660 |
| $K_2CO_3$ $D_{90}$ (μm) | −0.0601051 |
| Reaction temperature (° C.) | 0.925500 |
| TATD * $K_2CO_3$ $D_{90}$ | −0.0478972 |
| TATD * Temperature | −0.445000 |
| MsCl * $K_2CO_3$ (equiv) | 13.7500 |
| MsCl * $K_2CO_3$ $D_{90}$ | −0.0277453 |
| MsCl * Temperature | −0.225000 |
| $K_2CO_3$ (equiv) * $K_2CO_3$ $D_{90}$ | 0.135514 |
| Center point | 3.01717 |

The coefficients in the table above were be combined in a regression equation (shown below), which was then used to generate the overlaid contour plots seen in FIGS. 5, 6, 7, 8, 9, and 10. Parameters not shown in contour plots were held constant at the middle of the range used in the study.

1.5 hr Conversion (%)=129.8+3.87TATD(eq)−12.47MSCl(eq)−35.6$K_2CO_3$(eq)−0.0612$K_2CO_3$(d90)+0.926Rxn. Temp. (° C.)−0.0479TATD(eq)*$K_2CO_3$(d90)−0.445TATD(eq)*Rxn. Temp. (° C.)+13.75MsCl(eq)*$K_2CO_3$(eq)−0.0277MSCl(eq)*$K_2CO_3$(d90)−0.225MsCl(eq)*Rxn. Temp. (° C.)+0.1355$K_2CO_3$(eq)*$K_2CO_3$(d90)

FIG. 5 is a graph that summarizes the main effects of the reaction parameters determined to have the greatest impact on reaction conversion of TATD (compound (I)) to TATD-Ms (compound (Ib)) for up to 1.5 hours according to the reaction scheme shown in FIG. 2. The reaction parameters studied include: molar equivalent ratios of TATD, methanesulfonyl chloride, and potassium carbonate; mesh size and D90 of potassium carbonate particles; and reaction temperature. These effects are represented by the length of the line between two dots in FIG. 5. As disclosed herein, the conversion of compound (I) to compound (Ib) was greatly affected when the molar equivalent ratio of potassium carbonate was between 0.9 and 1.3 and the size of the potassium carbonate particles had a D90 between 36 and 250. The conversion of compound (I) into compound (Ib) was not as greatly affected when the molar equivalent ratio of compound (I) was between 0.9 and 1.3), or when equivalent ratio of methanesulfonyl chloride was between 1.8 and 2.6) and reaction temperature was between −5 degrees C. and 20 degrees C.).

Figure 6:
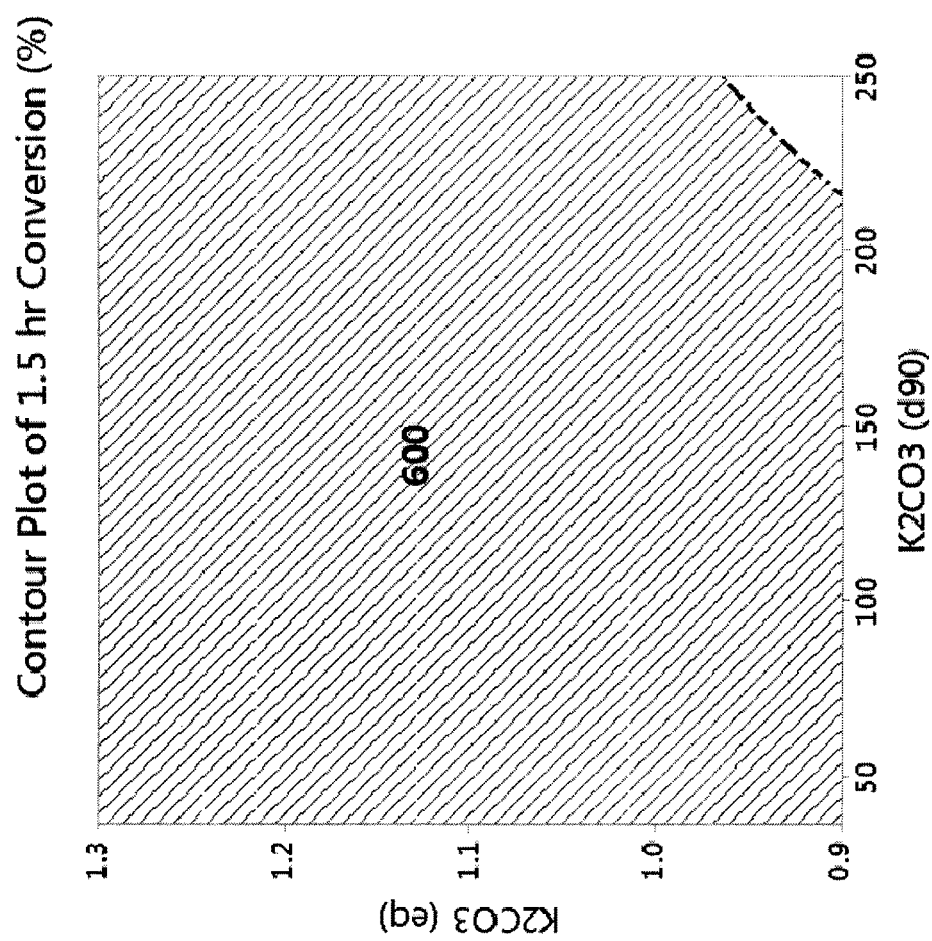
FIG. 6 is the contour plot of reaction conversion at 1.5 hours versus potassium carbonate particle size and equivalents. Y-axis shows the number of equivalents of potassium carbonate ("K2CO3 (eq)") relative to compound (II); x-axis shows the D90 values of potassium carbonate in micrometers ("K2CO3 (d90)").

FIG. 6 is a contour plot of reaction conversion of compound (I) to compound (Ib) at 1.5 hours versus potassium carbonate particle size and equivalents of potassium carbonate. As disclosed herein, the contour plot shows that the reaction conversion of compound (I) to compound (Ib) was greater than 90% (represented by the shaded region labeled as 600). The unshaded region in the lower right corner of this contour plot shows that the conversion of compound (I) to compound (Ib) was less than 90% when the particle size of potassium carbonate had a D90 of greater than 217 μm, and when the molar equivalent ratio of potassium carbonate was less than 0.96 equivalents.

FIG. 7 is a contour plot of reaction conversion of compound (I) to compound (Ib) at 1.5 hours versus potassium carbonate particle size and reaction temperature. As disclosed herein, the contour plot shows that the reactions using a potassium carbonate particle size of, for example, less than 400 μm resulted in greater than 90% reaction conversion (the shaded area labeled as 700), when the reaction temperature was controlled between, for example, −5 and 20 degrees C.), and when the equivalents of the other components were set to their respective optimal values.

FIG. 8 is a contour plot of reaction conversion of compound (I) to compound (Ib) at 1.5 hours versus potassium carbonate particle size and molar equivalents of methanesulfonyl chloride. As disclosed herein, the contour plot shows that the area labeled as 800 represents greater than 90% reaction conversion of compound (I) to compound (Ib). The unshaded area in the upper right corner of the contour plot shows that the reactions resulted in less than 90% conversion of compound (I) to compound (Ib) when the molar equivalents of methanesulfonyl chloride were greater than 2.2 and when the potassium carbonate particle size was selected at a D90 close to 400.

FIG. 9 is a contour plot of reaction conversion at 1.5 hours versus potassium carbonate particle size and compound (I) molar equivalents. As disclosed herein, the contour plot shows the area labeled as 900, which represents reaction conversion of greater than 90%. Low reaction conversion (for example less than 90%) of compound (I) to compound (Ib) was observed with very high molar equivalents of compound (I) (for example greater than 1.1) and with D90 greater than or equal to 400; the undesirably poor conversion is shown by the unshaded area in the upper right corner of the FIG. 9.

FIG. 10 is a contour plot of the temperature spike after potassium carbonate charge versus potassium carbonate particle size and reaction temperature. As disclosed herein, the region labeled as 1000 represents the reaction conditions that resulted in a controlled batch temperature spike of less than 5 degrees C., and the shaded area indicates a rise in the temperature by more than 5 degrees C. For example, reactions using potassium carbonate with a small particle size and high reaction temperature resulted in batch temperature spikes greater than 5 degrees C. In contrast, reactions using potassium carbonate with a particle size at, for example, D90 of 100-400 did not result in batch temperature spikes greater than 5 degrees C., even when the reaction was carried out at the high reaction temperature, e.g., 10 degrees C.

TATD-Ms (compound (Ib)) obtained based on the design of experiments studies (DOE) and from the process disclosed herein can be further reacted with ACLE (i.e., compound (II)) to yield TATD-CLE (i.e., compound (III)), as shown in FIG. 1c. Compound (III) can be further reacted with pyrazolyl urea intermediate (IV). The synthesis of pyrazolyl urea intermediate (IV) is disclosed in "Synthesis and SAR of novel parenteral anti-pseudomonal cephalosporins: Discovery of FR264205," *Bioorganic & Medicinal Chemistry Letters,* 18, 4849-4852 (2008). Treatment of 5-amino-1-methylpyrazole (i.e., compound (Ic)) with $NaNO_2/HCl$ in water at 5 degrees C. gives the 4-nitrosopyrazole derivative, which can be reduced to the diaminopyrazole (Id) by catalytic hydrogenation over Pd/C in the presence of $H_2SO_4$. Selective acylation of the 4-amino group of compound (Id) with phenyl chloroformate in the presence of NaOH in $H_2O$/dioxane at 10° C. then yields the phenyl carbamate (i.e., compound (Ie)). After protection of the free amine group of carbamate compound (Ie) with chlorotriphenylmethane in the presence of triethylamine in THF, the resulting N-trityl derivative (compound (If)) can be coupled with N-Boc-ethylenediamine (M) in the presence of triethylamine in DMF to afford pyrazolyl urea (IV).

6.4. Pharmaceutical Compositions

Ceftolozane (including pharmaceutically acceptable salts thereof such as ceftolozane sulfate) can be formulated as a pharmaceutical composition. The pharmaceutical composition can optionally further include a beta-lactamase inhibitor such as tazobactam. The ceftolozane can be obtained by processes described herein. In particular, pharmaceutical compositions can be obtained by a process comprising the step of forming an aqueous solution containing ceftolozane, and lyophilizing the aqueous solution to obtain a pharmaceutical composition. The aqueous solution may additionally comprise excipients, stabilizers, pH adjusting additives (e.g., buffers) and the like. Non-limiting examples of these additives include sodium chloride, citric acid and L-arginine. For example, the use of sodium chloride can result in greater stability; L-arginine can be used to adjust pH and to increase the solubility of ceftolozane; and citric acid can be used to prevent discoloration of the product, due to its ability to chelate metal ions. In particular, the aqueous solution can include ceftolozane sulfate and additional components such as sodium chloride to stabilize the ceftolozane, and an alkalizing agent such as L-arginine to provide a pH of about 5-7 prior to lyophilization. The pharmaceutical compositions can be lyophilized (freeze-dried) and stored as a lyophilate for later reconstitution. Exemplary disclosures relating to lyophilization of pharmaceutical formulations include Konan et al., Int. J. Pharm. 2002 233 (1-2), 293-52; Quintanar-Guerreo et al., J. Microencapsulation 1998 15 (1), 107-119; Johnson et al., J. Pharmaceutical Sci. 2002, 91 (4), 914-922; and Tang et al., Pharmaceutical Res. 2004, 21 (4), 191-200; the disclosures of which are incorporated herein by reference. As an alternative to lyophilization, a pharmaceutical composition can be spray dried, or stored frozen and then thawed, reconstituted, and diluted before administration.

In some embodiments, the pharmaceutical composition of the disclosure, e.g., comprising a compound of formula (Z-VI), e.g., a compound of formula (VI), is formulated as a pharmaceutically acceptable salt. The term "pharmaceutically acceptable salt" refers to the relatively non-toxic, inorganic and organic acid addition salts of a compound of formula (Z-Vb) or a compound of formula (Z-VI). These salts can be prepared in situ during the final isolation and purification of the compound, or by separately reacting a purified compound in its free base form with a suitable organic or inorganic acid, and isolating the salt thus formed. Representative salts include the hydrobromide, hydrochloride, hydrogen sulfate (also known as the sulfate), bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulfonate salts, and amino acid salts, and the like. See, for example, Berge et al. 1977, "Pharmaceutical Salts," J. Pharm. Sci. 66: 1-19.

Pharmaceutical compositions of the cephalosporin compounds of the disclosure, e.g., a compound of formula (Z-VI), e.g., a compound of formula (VI), can be prepared for storage as lyophilized formulations or aqueous solutions by admixing the pharmaceutically active ingredient having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980).

In some embodiments, buffering agents are used to help to maintain the pH in the range that approximates physiological conditions from about 2 mM to about 50 mM. For example, one or more buffering agents can be present at a concentration of about 2, about 5, about 10, about 30, or about 50 mM. Suitable buffering agents for use with the present disclosure include both organic and inorganic acids and salts thereof, such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

In some embodiments, preservatives are added in amounts ranging from 0.01%-1% (w/v). For example, a preservative in an amount of about 0.02%, about 0.05%, about 0.1%, about 0.2%, about 0.5%, about 0.8% (w/v) can be added. Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol.

In some embodiments, isotonifiers sometimes known as "stabilizers" are added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as thiourea, glutathione, thioctic acid, sodium thioglycolate, thioglycerol, α-monothioglycerol and sodium thiosulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. In some embodiments, stabilizers are present in the range from 0.1 to 10,000 weights per part of weight of pharmaceutically active ingredient, such as 0.1 to 1,000, 0.2 to 2,000, 0.5 to 5,000, 1 to 10,000, or 1 to 1,000 weights per part of weight of pharmaceutically active ingredient. For example, stabilizers can be present in about 0.2, about 0.5, about 10, about 100, about 1,000, or about 8,000 weights per part of weight of pharmaceutically active ingredient.

In some embodiments, non-ionic surfactants or detergents (also known as "wetting agents") are added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). In some embodiments, non-ionic surfactants are present in a range of from about 0.05 mg/mL to about 1.0 mg/mL. For instance, non-ionic surfactants can be present in about 0.05, about 0.07, about 0.08, about 0.1, about 0.2, about 0.3, about 0.4, about 0.5, about 0.6, about 0.8, or about 1.0 mg/mL.

Additional miscellaneous excipients include bulking agents (e.g., starch), chelating agents (e.g., EDTA), antioxidants (e.g., ascorbic acid, methionine, vitamin E), and cosolvents.

The compositions will usually be supplied as part of a sterile, pharmaceutical composition that will normally include a pharmaceutically acceptable carrier. This composition can be in any suitable form (depending upon the desired method of administration). For example, the pharmaceutical composition can be formulated as an aqueous solution and administered by intravenous injection or intravenous infusion.

Pharmaceutical compositions can include ceftolozane obtained by methods described herein, combined with a beta-lactamase inhibitor, such as tazobactam (CAS#: 89786-04-9), avibactam (CAS#1192500-31-4), Sulbactam (CAS#68373-14-8) and/or clavulanic acid (CAS#58001-44-8). The beta lactamase inhibitor can be included in a crystalline or amorphous form, such as a lyophilized tazobactam or crystalline tazobactam (e.g., U.S. Pat. Nos. 8,476,425 and 5,763,603) to obtain the pharmaceutical composition.

Pharmaceutical compositions comprising ceftolozane can be formulated to treat infections by parenteral administration (including subcutaneous, intramuscular, and intravenous) administration. In one particular embodiment, the pharmaceutical compositions described herein are formulated for administration by intravenous injection or infusion. Pharmaceutical antibiotic compositions can include ceftolozane sulfate and stabilizing amount of sodium chloride (e.g., 125 to 500 mg of sodium chloride per 1,000 mg ceftolozane active) in a lyophilized unit dosage form (e.g., powder in a vial). The unit dosage form can be dissolved with a pharmaceutically acceptable carrier, and then intravenously administered. In another aspect, pharmaceutical antibiotic compositions can include ceftolozane sulfate obtained by a process comprising the steps of lyophilizing an aqueous solution containing ceftolozane and a stabilizing amount of sodium chloride, where the stabilizing amount of sodium chloride is about 125 to 500 mg of sodium chloride per 1,000 mg ceftolozane active in the aqueous solution prior to lyophilization.

6.5. Methods of Treatment

In one aspect, provided herein is a method for the treatment of bacterial infections in a mammal, comprising administering to said mammal a therapeutically effective amount of a pharmaceutical composition comprising ceftolozane prepared according to one or more of the methods described herein. A method for the treatment of bacterial infections in a mammal can comprise administering to said mammal a therapeutically effective amount of a pharmaceutical composition comprising ceftolozane sulfate and sodium chloride.

As used herein, a "mammal" can be any mammal, such as a mouse, a rat, a dog, a cat, a horse, a pig, a cow, or a primate, such as a human. In certain embodiments, the mammal is a human. The mammal can be an adult or a juvenile mammal.

The pharmaceutical compositions can used in combination with metronidazole for the treatment of complicated intra-abdominal infections caused by the following Gram-negative and Gram-positive microorganisms such as: *Escherichia coli* (including strains producing CTX-M-14/15 ESBLs), *Klebsiella pneumoniae* (including strains producing CTX-M-15 ESBLs), *Pseudomonas aeruginosa, Enterobacter cloacae, Klebsiella oxytoca, Proteus mirabilis, Bacteroides fragilis, Bacteroides ovatus, Bacteroides thetaiotaomicron, Bacteroides vulgatus, Streptococcus anginosus, Streptococcus constellatus*, and *Streptococcus salivarius*.

The pharmaceutical compositions can used for the treatment of complicated urinary tract infections, including pyelonephritis, with or without concurrent bacteremia, caused by the following Gram-negative microorganisms: *Escherichia coli* (including strains resistant to levofloxacin and/or producing CTX-M-14/15 ESBLs), *Klebsiella pneumoniae* (including strains resistant to levofloxacin and/or producing CTX-M-15 ESBLs), *Proteus mirabilis*, and *Pseudomonas aeruginosa*.

The recommended dosage regimen of pharmaceutical compositions comprising ceftolozane prepared by one or more methods disclosed herein, and tazobactam in an amount providing 1 g of ceftolozane active per 500 mg of tazobactam acid, is 1.5 g administered every 8 hours by intravenous (IV) infusion over 1 hour in patients ≥18 years of age. The duration of therapy should be guided by the severity and site of infection and the patient's clinical and bacteriological progress (e.g., every 8 hours for 4-14 days for complicated Intra-Abdominal Infections and 7 days for Complicated Urinary Tract Infections, including Pyelonephritis).

7. EXAMPLES

Example 1: Preparation of (Z)-2-(5-amino-1,2,4-thiadiazol-3-yl)-2-(((1-(tert-butoxy)-2-methyl-1-oxopropan-2-yl)oxy)imino) acetic methanesulfonic anhydride (TATD-Ms)

Preparation of TATD-Ms

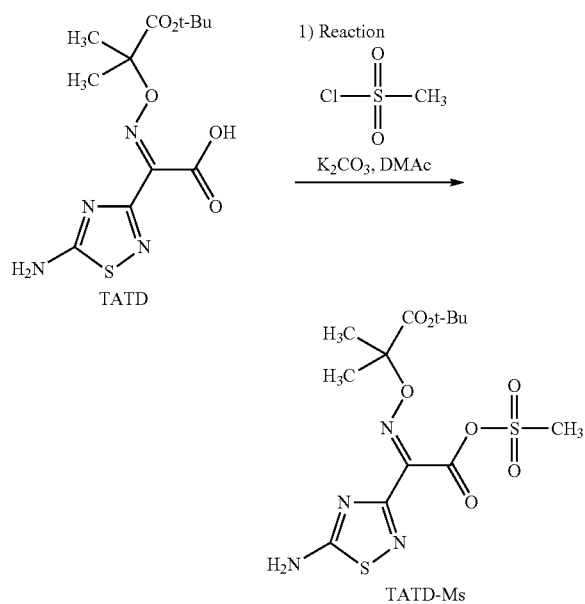

Reactor 1 was charged with anhydrous DMAc [N,N-dimethylacetamide] (281 g, 300 mL, 6.0 volumes) followed by TATD (44.8 g, 136 mmol, 1.1 equiv) at ambient temperature (20-25 deg C.), and the batch was stirred until all solids were dissolved, as evidenced by visual inspection. The batch was cooled to a temperature between 0 and 10° C. (target temperature was 5° C.). Then reactor 1 was charged with methanesulfonyl chloride [methane sulfonyl chloride] (31.1 g, 21.0 mL, 271 mmol, 2.2 equiv) over the course of 10 to 15 minutes (9 to 13 equiv/h), while maintaining the batch temperature between 3 and 7° C. (target temperature was 5° C.). Then potassium carbonate (18.8 g, 135.7 mmol, 1.1 equiv) was added to reactor 1 in one portion. The batch was agitated for 1 hour, while keeping the temperature between 3 and 7° C. (target temperature was 5° C.). Subsequently, reactor 1 was charged with ethyl acetate (449 g, 500 mL, 10 volumes) at a rate of 3.7 to 10 vol/h, and the batch was cooled to a temperature between −5 and 0° C. (target temperature was −3° C.).

The batch in reactor 1 was charged with a 2.4% HCl solution (270 mL) at a rate of 3 to 5 vol/h, while maintaining the batch at a temperature between −5 and 0° C. (target temperature was −3° C.) throughout the addition. The batch was agitated for 10 to 30 minutes, while maintaining the batch at a temperature between −5 and 0° C. The phases were allowed to separate, and the upper organic phase was collected.

The batch in reactor 1 was charged with a 10% (w/v) sodium chloride solution (400 mL) sodium chloride aqueous solution, while maintaining the batch at a temperature between −5 and 0° C. (target temperature was −3° C.) throughout the addition. The batch was agitated for 10 to 30 minutes, while maintaining the temperature between −5 and 0° C. (target −3° C.). The phases were allowed to separate, and the upper organic phase was collected. The batch was carried on to the next step without further work-up or purification.

Referring to FIG. 11, $^1$H-NMR spectrum of compound of formula (Ib) TATD-Ms shows signals for methyl protons on methanesulfonate at position (18), signals for dimethyl protons at position (15, 16), tert-butyl protons at position (24, 25, 26) and amino group at position 6.

$^1$H-NMR 400 MHz, (CDCl$_3$) 1.47 (9H, s), 1.58 (6H, s), 3.51 (3H, s), 7.95 (2H, s).

While not required, the methods disclosed herein allow for the isolation of a compound of formula (Z-Ib), e.g., compound (Ib), at high yield and/or high purity.

Example 2: Synthesis of Compound (III) from Compound (I), with Greater than 90% Yield Using the preferred methods described herein, 403.2 kg of compound (I) was converted to 789.2 kg of compound (III), (TATD-CLE), a 93.79% yield. The conversion of compound (I) to compound (Ib) was performed by reacting compound (I) with methanesulfonyl chloride and potassium carbonate. The conversion of compound (Ib) to compound (III) was performed by reaction of compound of formula (Ib) with ACLE com pound of formula (II). The details of this synthesis procedure are disclosed below.

TATD compound of formula (I) (403.2 kg) was dissolved in DMAc (2,600 L) at 20° C. The solution was cooled to 0-10° C., and then methanesulfonyl chloride (280 kg) was added in 10 to 20 minutes followed by potassium carbonate (170 kg). The reaction was stirred at 0-10° C. for 1 hour then diluted with ethyl acetate (3,800 L) and washed with 0.4 N HCl solution (2,440 L) and then a 10% sodium chloride solution (3,600 L). This organic solution was added to a biphasic mixture of ACLE compound of formula (II) (461.5 kg), water (1350 L) and ethyl acetate (1350 L) at 0-5° C. The pH of the reaction was continuously measured and maintained at a pH of 2 to 4 using triethylamine. The reaction was stirred for 30 minutes and sodium chloride (45 kg) was added and stirred for an additional 40 minutes. The lower aqueous layer was separated and discarded. The ethyl acetate solution was washed with 20% sodium chloride solution (1,350 L). The organic solution was separated and concentrated to 1,350 L, then TATD-CLE seed (18 kg) was added and the product was isolated and dried to provide 779.5 kg of TATD-CLE compound of formula (III) as a white solid.

Calculation of the yield of the product was performed as shown below.
403.2 kg TATD/330.36 MW TATD=1.22 moles of TATD×681.18 MW TATD-CLE=theoretical yield 831.37 kg
779.5 kg TATD-CLE/831.37 theoretical yield=93.7% yield
704.0 kg TATD-CLE (using potency of 89.2% TATD-CLE)/831.37 theoretical yield=84.7% yield
704.0 kg TATD-CLE/756.3 theoretical yield=93.1% yield (from ACLE, potency corrected)

(Comparative) Example 3: Synthesis of Compound (III) with Less than 80% Yield U.S. Pat. No. 7,129,232, column 20, line numbers 35-55, discloses the following example of converting compound (I) to compound (III) with a 77.4% yield. The detailed synthesis procedure from this first comparative example is disclosed below.

A mixture of N,N-dimethylformamide (0.648 ml) and phosphoryl chloride (0.781 ml) was stirred at room temperature for 30 minutes. To the mixture were added tetrahydrofuran (4 ml) and (Z)-2-{5-[(tert-butoxycarbonyl)amino]-1,2,4-thiadiazol-3-yl}[(2-tert-buto-xy-1,1-dimethyl-2-oxoethoxy)imino]ethanoic acid compound of formula (I) (3 g) at 4° C., and the reaction mixture was stirred at room temperature for 1 hour. Meanwhile, a mixture of benzhydryl 7β-amino-3-chloromethyl-3-cephem-4-carboxylate hydrochloride (3 g) and N-(trimethylsilyl)acetamide compound of formula (II) (8.72 g) in tetrahydrofuran (15 ml) was warmed to make a clear solution. The solution was then cooled to −20° C. and added to the activated acid solution obtained above. The reaction mixture was stirred at a temperature of −10° C. to 0° C. for 1 hour and poured into a mixture of ethyl acetate and water. The aqueous layer was separated, and the organic layer was washed with brine, dried over anhydrous magnesium sulfate and filtered. The filtrate was concentrated in vacuo and purified by column chromatography on silica gel eluting with hexane/ethyl acetate (3:2) to give benzhydryl 7β-[(Z)-2-(5-tert-butoxycarbonylamino-1,2,4-thiadiazol-3-yl)-2-(1-tert-butoxycarbonyl-1-methylethoxyimino)acetamido]-3-chloromethyl-3-cephem-4-carboxylate compound of formula (III) (4.79 g), 77.4% yield.

(Comparative) Example 4: Synthesis of Compound (III) with Less than 80% Yield

U.S. Pat. No. 7,192,943, column 20, line numbers 5-35, discloses the following example of converting compound (I) to compound (III) with a 75.4% yield. The detailed synthesis procedure from this second comparative example is disclosed below.

To a solution of (Z)-2-(5-amino-1,2,4-thiadiazol-3-yl)-2-(1-tert-butoxycarbonyl-1-methylethoxyimino)acetic acid compound (I) (319 g) in N,N-dimethylacetamide (1.5 L) were added potassium carbonate (113 g) and methanesulfonyl chloride (126 ml) under ice-cooling. The mixture was stirred at 10 degrees C. for 2 hours. The reaction mixture was added to a mixture of ethyl acetate and water. The organic layer was washed with water and brine to give an activated acid solution. On the other hand, a suspension of 4-methoxybenzyl 7β-amino-3-chloromethyl-3-cephem-4-carboxylate hydrochloride compound of formula (II) (300 g) in a mixture of water (1 L) and ethyl acetate (1 L) was adjusted to pH 6 with triethylamine under ice-cooling. To the resulting mixture was dropwise added the above obtained activated acid solution at 10 degrees C. under stirring. Stirring was continued at 5-10 degrees C. for 1.5 hours keeping pH of the reaction mixture at 6 with triethylamine. The organic layer was separated, washed with water and brine, and evaporated in vacuo. The concentrate was poured into diisopropyl ether (15 L), and the resulting precipitate was collected by filtration and dried to give 4-methoxybenzyl 7β-[(Z)-2-(5-amino-1,2,4-thiadiazol-3-yl)-2-(1-tert-butoxycarbonyl-1-methylethoxyimino)acetamido]-3-chloromethyl-3-cephem-4-carboxylate (compound of formula (III)) (495.7 g), 75.4% yield.

8. EQUIVALENTS AND INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:
1. A process for preparing a compound of formula (Z-Ib-1):

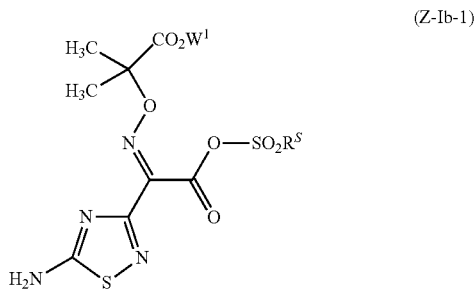

wherein:
$W^1$ is an acid-labile protecting group,
$X^1$ is Cl, Br, or I, and
$R^S$ is a $C_1$-$C_6$ alkyl;
which comprises admixing a compound of formula (Z-I):

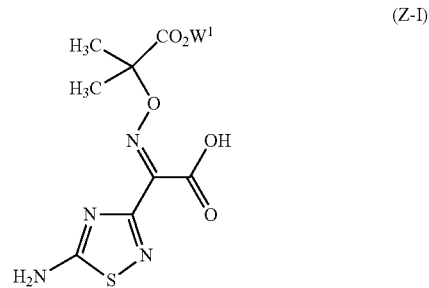

with a compound of formula $R^S SO_2 X^1$,
in the presence of alkali metal carbonate particles having at least about 50% of the particles by weight in a range of from about 70 to about 250 micrometers,
to give the compound of formula (Z-Ib-1).

2. The process of claim 1, wherein the alkali metal carbonate particles have at least about 70% of the particles by weight in a range of from about 70 to about 250 micrometers.

3. The process of claim 1, wherein the alkali metal carbonate particles have at least about 80% of the particles by weight in a range of from about 70 to about 250 micrometers.

4. The process of claim 1, wherein the alkali metal carbonate particles have at least about 90% of the particles by weight in a range of from about 70 to about 250 micrometers.

5. The process of claim 1, wherein the alkali metal carbonate is potassium carbonate.

6. The process of claim 1, wherein $W^1$ is tert-butyl.

7. The process of claim 1, wherein $R^S$ is $CH_3$.

8. The process of claim 1, wherein the molar equivalent ratio of the compound of formula (Z-I) to the alkali metal carbonate is in a range of from about 0.6 to about 1.4.

9. The process of claim 1, wherein the reaction temperature is in a range of from about −5 to about 20° C.

10. The process of claim 1, wherein $X^1$ is Cl.

11. The process of claim 1, wherein the molar equivalent ratio of the compound of formula $R^SSO_2X^1$ to the compound of formula (Z-I) is in a range of from about 1.3 to about 3.0.

12. The process of claim 1, further comprising reacting the compound of formula (Z-Ib-1) with a compound of formula (Z-II):

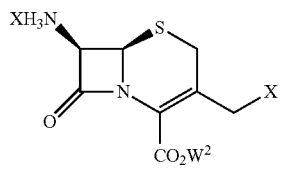
(Z-II)

to give a compound of formula (Z-III):

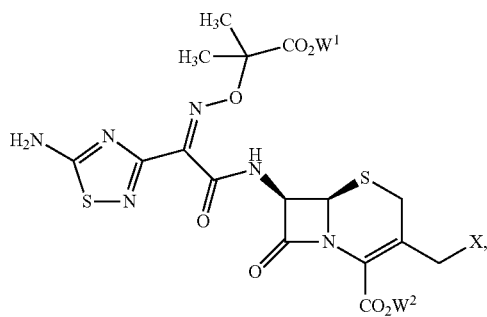
(Z-III)

wherein:
X is Cl, Br, or I; and
$W^2$ is tert-butyl, para-methoxybenzyl, ortho-methoxybenzyl, or diphenylmethyl.

13. The process of claim 12, further comprising reacting the compound of formula (Z-III) with a compound of formula (Z-IV):

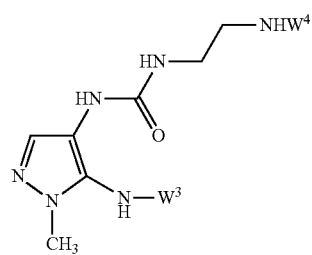
(Z-IV)

to give a compound of formula (Z-V):

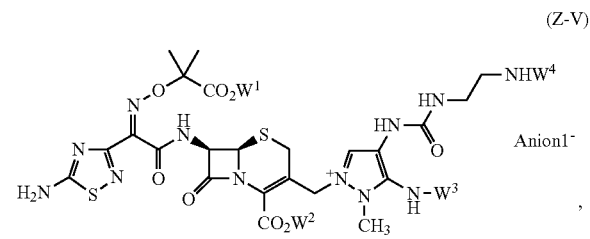
(Z-V)

wherein:
$W^3$ and $W^4$ are each independently triphenylmethyl, tert-butyl, tert-butoxycarbonyl, or para-methoxybenzoyl; and
Anion1 is Cl, Br, I, trifluoroacetate, trifluoromethanesulfonate, or hydrogen sulfate.

14. The process of claim 13, further comprising converting the compound of formula (Z-V):

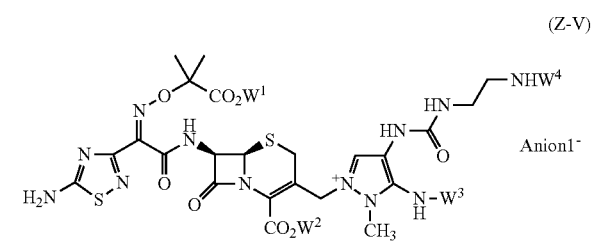
(Z-V)

to a compound of formula (Z-VI):

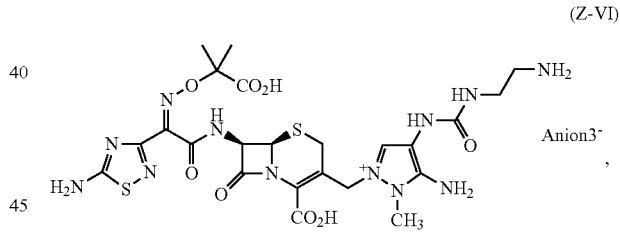
(Z-VI)

wherein
Anion3 is Cl, Br, I, methanesulfonate, toluenesulfonate, hydrogen sulfate, or sulfate.

15. The process of claim 1, comprising reacting a compound (I):

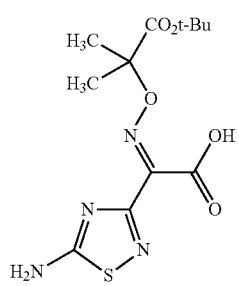
(I)

with methanesulfonyl chloride in the presence of potassium carbonate particles having a D90 of 70-250 micrometers, to obtain a compound (Ib):

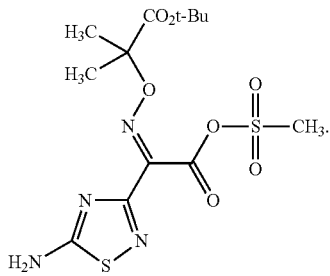
(Ib)

16. The process of claim 15, wherein a total of about 1.05 to 1.30 equivalents of potassium carbonate are combined with compound (I).

17. The process of claim 15, wherein the reaction of compound (I) occurs in a solution at a temperature of about 0-13 degrees C.

18. The process of claim 15, wherein:
   (a) a total of about 1.05 to 1.30 equivalents of potassium carbonate are combined with compound (I); and
   (b) the reaction of compound (I) occurs in a solution at a temperature of about 0-13 degrees C.

19. The process of claim 18, wherein at least about 90% of compound (I) is converted to compound (Ib).

20. The process of claim 15, wherein the process further comprises reacting compound (Ib) with compound (II):

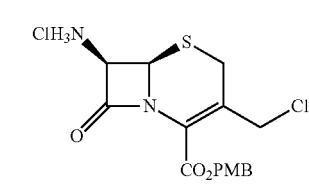
(II)

to give compound (III):

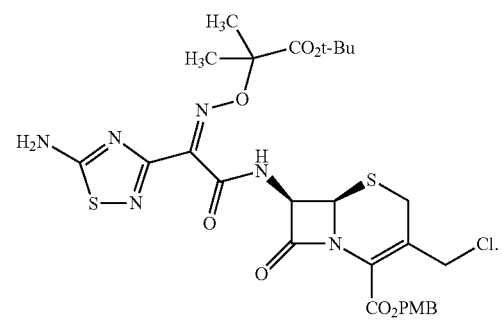
(III)

21. The process of claim 20, wherein the process further comprises reacting compound (III) with compound (IV):

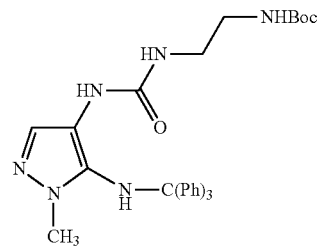
(IV)

to give compound (V):

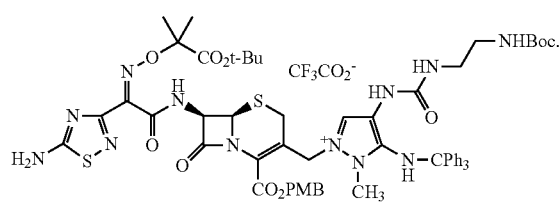
(V)

22. The process of claim 21, wherein the process further comprises converting compound (V):

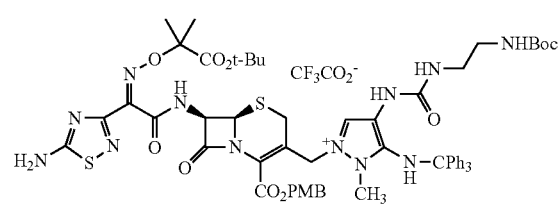
(V)

to compound (VI):

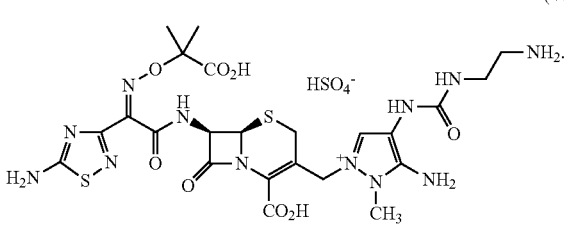
(VI)

23. A process comprising reacting compound (I):

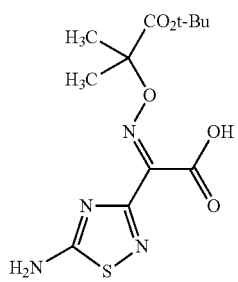
(I)

with methanesulfonyl chloride in the presence of an amount of potassium carbonate particles having a predetermined D90 and at a temperature effective to provide at least 90% conversion of compound (I) to compound (Ib):

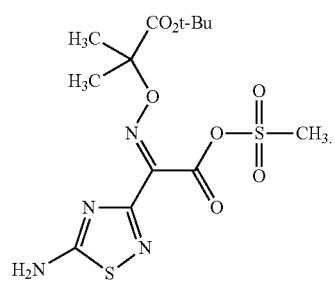
(Ib)

24. The process of claim 23, wherein the reaction is performed at a temperature of about 0 to 15 degrees C.

25. The process of claim 23, wherein the reaction is performed without an increase in temperature of greater than about 10 degrees C.

26. The process of claim 23, wherein the reactants are maintained in contact for about 3 hours before isolating the compound (Ib).

27. The process of claim 23, wherein at least about 97% of compound (I) is converted to compound (Ib) within about 3 hours.

28. The process of claim 23, wherein the molar ratio of potassium carbonate to compound (I) is between about 1.05 and 1.30 in the reaction.

29. The process of claim 23, wherein:
(a) the reaction is performed at a temperature of about 0 to 15 degrees C., and the reaction is performed without an increase in temperature of greater than about 10 degrees C.;
(b) the reaction is performed within about 1-3 hours;
(c) at least about 97% of compound (I) is converted to compound (Ib); and
(d) the molar ratio of potassium carbonate to compound (I) is between about 1.05 and 1.30 in the reaction.

30. A composition comprising compound (I):

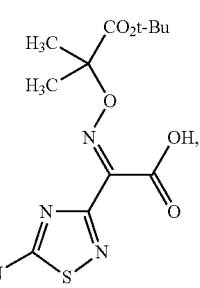
(I)

methanesulfonyl chloride, and potassium carbonate particles having a D90 of 70-180 micrometers.

31. The composition of claim 30, comprising a total of about 1.05 to 1.30 equivalents of potassium carbonate relative to the amount of the compound (I).

32. The composition of claim 30, having a temperature of about 0 to 15 degrees C.

33. The composition of claim 30, further comprising compound (Ib):

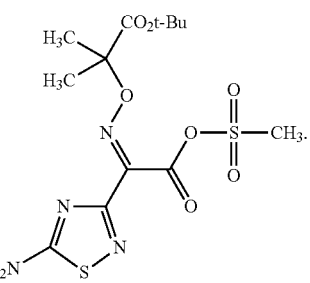
(Ib)

* * * * *